(12) United States Patent
McGillicuddy

(10) Patent No.: US 12,134,092 B2
(45) Date of Patent: Nov. 5, 2024

(54) APPARATUS AND METHOD FOR CENTRIFUGING A BIOLOGIC

(71) Applicant: Cervos Medical LLC, Marshfield, MA (US)

(72) Inventor: Andrew McGillicuddy, Humarock, MA (US)

(73) Assignee: Cervos Medical LLC, Avon, MA (US)

( * ) Notice: Subject to any disclaimer, the term of this patent is extended or adjusted under 35 U.S.C. 154(b) by 39 days.

(21) Appl. No.: 16/767,863

(22) PCT Filed: Nov. 30, 2018

(86) PCT No.: PCT/US2018/063317
§ 371 (c)(1),
(2) Date: May 28, 2020

(87) PCT Pub. No.: WO2019/108937
PCT Pub. Date: Jun. 6, 2019

(65) Prior Publication Data
US 2020/0360921 A1    Nov. 19, 2020

(51) Int. Cl.
*B01L 3/00*      (2006.01)
*A61M 1/36*      (2006.01)

(52) U.S. Cl.
CPC ......... *B01L 3/5021* (2013.01); *A61M 1/3696* (2014.02); *B01L 3/5635* (2013.01);
(Continued)

(58) Field of Classification Search
None
See application file for complete search history.

(56) References Cited

U.S. PATENT DOCUMENTS

| 4,058,252 A | 11/1977 | Williams |
| 4,120,662 A | 10/1978 | Fosslien |

(Continued)

FOREIGN PATENT DOCUMENTS

| EP | 2407245 A2 | 1/2012 |
| KR | 10-1333789 B1 | 11/2013 |

(Continued)

OTHER PUBLICATIONS

Duregger, K., et al., Influence of storage conditions on the release of growth factors in platelet-rich blood derivative, Current Directions in Biomedical Engineering 2016; 2(1) 311-314.

(Continued)

*Primary Examiner* — Lore R Jarrett
(74) *Attorney, Agent, or Firm* — Hamilton, Brook, Smith & Reynolds, P.C.

(57) ABSTRACT

A device and associated method for centrifuging a physiological fluid includes a syringe including a tip, a base and a barrel extending between the tip and the base to hold a physiological fluid. The syringe includes a plunger positioned within the barrel and the plunger includes a plunger seal in sealing engagement with an inside wall of the barrel. An exoskeleton is provided to support the syringe at least partially within the exoskeleton for use in a centrifuge. The syringe is removably coupled to the exoskeleton using an interference fit. The method includes holding the physiological fluid in the syringe, supporting the syringe at least partially within the exoskeleton, and centrifuging the physiological fluid in the syringe supported by the exoskeleton.

24 Claims, 24 Drawing Sheets

(52) U.S. Cl.
CPC ... *B01L 2200/025* (2013.01); *B01L 2200/026* (2013.01); *B01L 2300/0681* (2013.01); *B01L 2400/0409* (2013.01)

(56) References Cited

U.S. PATENT DOCUMENTS

| | | | |
|---|---|---|---|
| 4,142,668 | A | 3/1979 | Lee |
| 4,152,270 | A | 5/1979 | Cornell |
| 4,154,690 | A | 5/1979 | Ballies |
| 4,443,345 | A | 4/1984 | Wells |
| 4,809,860 | A | 3/1989 | Allen |
| 5,455,007 | A | 10/1995 | Calvo et al. |
| 5,474,687 | A * | 12/1995 | Van Vlasselaer ..... B01L 3/5021 422/534 |
| 5,555,920 | A | 9/1996 | Godolphin et al. |
| 5,707,331 | A | 1/1998 | Wells et al. |
| 6,123,655 | A | 9/2000 | Fell |
| 6,835,353 | B2 | 12/2004 | Smith et al. |
| 7,410,613 | B2 | 8/2008 | Iwaki et al. |
| 7,976,796 | B1 | 7/2011 | Smith et al. |
| 8,048,678 | B2 | 11/2011 | Duffy, Jr. et al. |
| 8,241,592 | B2 | 8/2012 | Duffy, Jr. et al. |
| 9,272,083 | B2 | 3/2016 | Duffy et al. |
| 9,421,319 | B2 | 8/2016 | Hwang |
| 10,005,081 | B2 | 6/2018 | Duffy et al. |
| 10,300,481 | B2 | 5/2019 | Pennie |
| 10,537,888 | B2 | 1/2020 | Pennie |
| 10,603,665 | B2 | 3/2020 | Levine et al. |
| 10,633,631 | B1 * | 4/2020 | Harris ............... C12N 5/0644 |
| 2004/0256331 | A1 | 12/2004 | Arking et al. |
| 2005/0124073 | A1 | 9/2005 | Freund |
| 2005/0274679 | A1 | 12/2005 | Kao et al. |
| 2006/0196885 | A1 | 9/2006 | Leach et al. |
| 2010/0112084 | A1 * | 5/2010 | Wu .................... C12N 5/0667 600/584 |
| 2010/0317099 | A1 * | 12/2010 | Leach .............. B01D 17/0217 435/325 |
| 2011/0086426 | A1 * | 4/2011 | Freund ................ C12M 47/04 435/308.1 |
| 2011/0124106 | A1 | 5/2011 | Froman |
| 2012/0052577 | A1 | 3/2012 | Espinosa et al. |
| 2014/0148325 | A1 * | 5/2014 | Jo ..................... A61M 1/3693 494/56 |
| 2014/0227732 | A1 * | 8/2014 | Saqi ..................... G01N 1/31 435/29 |
| 2015/0004079 | A1 | 1/2015 | Hassouneh et al. |
| 2015/0064687 | A1 | 3/2015 | Nemirovsky |
| 2015/0101995 | A1 * | 4/2015 | Kim ..................... B01D 63/02 210/259 |
| 2015/0367064 | A1 | 12/2015 | Pennie |
| 2016/0008808 | A1 * | 1/2016 | Levine ................ B01L 3/0282 422/522 |
| 2016/0106462 | A1 | 4/2016 | McGillicuddy |
| 2016/0158716 | A1 * | 6/2016 | Vos ..................... A61K 9/19 366/218 |
| 2018/0326413 | A1 * | 11/2018 | Walkowiak ........... B01L 3/5021 |
| 2020/0226812 | A1 | 7/2020 | Platzer et al. |
| 2020/0269256 | A1 * | 8/2020 | Ho ..................... A61K 9/0019 |
| 2020/0324285 | A1 | 10/2020 | Levine et al. |
| 2020/0360921 | A1 | 11/2020 | McGillicuddy |
| 2023/0010728 | A1 | 1/2023 | McGillicuddy |

FOREIGN PATENT DOCUMENTS

| | | |
|---|---|---|
| KR | 10-2014-0004890 A | 1/2014 |
| KR | 20-0471024 Y1 | 1/2014 |
| KR | 10-2014-0017948 A | 2/2014 |
| WO | 2002098566 A2 | 12/2002 |
| WO | 2005039773 A1 | 5/2005 |
| WO | 2007050986 A1 | 5/2007 |
| WO | 2010138895 A2 | 12/2010 |
| WO | 2014070804 A1 | 5/2014 |
| WO | 2014120797 A1 | 8/2014 |
| WO | 2015109100 A1 | 7/2015 |

OTHER PUBLICATIONS

International Search Report and Written Opinion for International Application No. PCT/2018/063317, titled "Apparatus and Method for Centrifuging a Biologic," Date of Mailing: Feb. 4, 2019.
International Preliminary Report on Patentability for International Application No. PCT/2018/063317, titled "Apparatus and Method for Centrifuging a Biologic," Date of Issuance Jun. 2, 2020.
Fukaya, M. and Ito, A., "A New Economic Method for Preparing Platelet-rich Plasma," PRS Go, pp. 1-7 (2014).

* cited by examiner

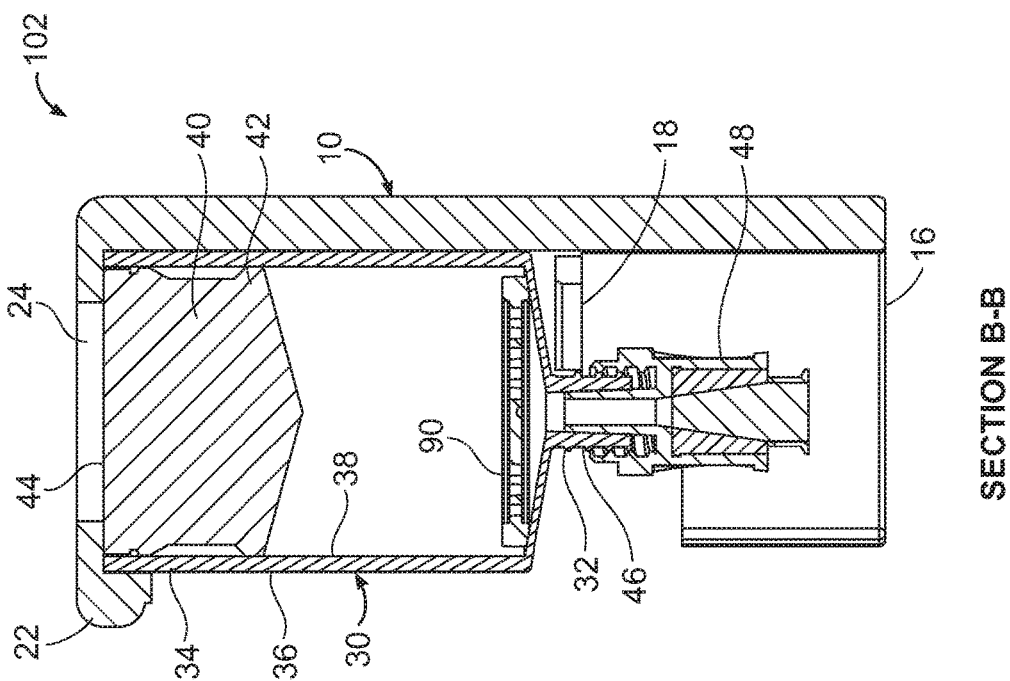
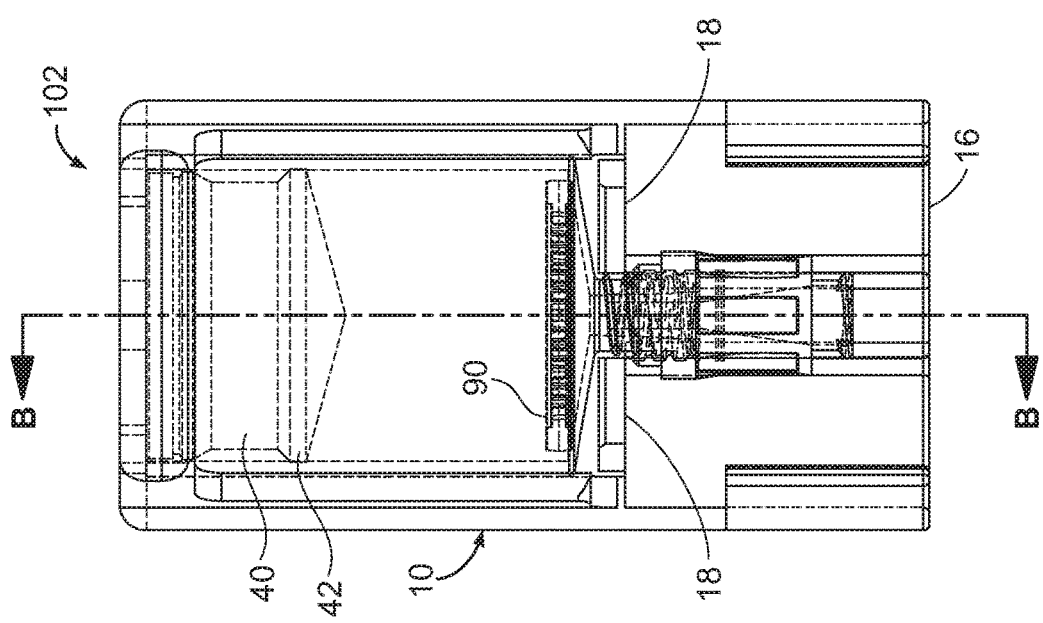
FIG. 1E
FIG. 1D

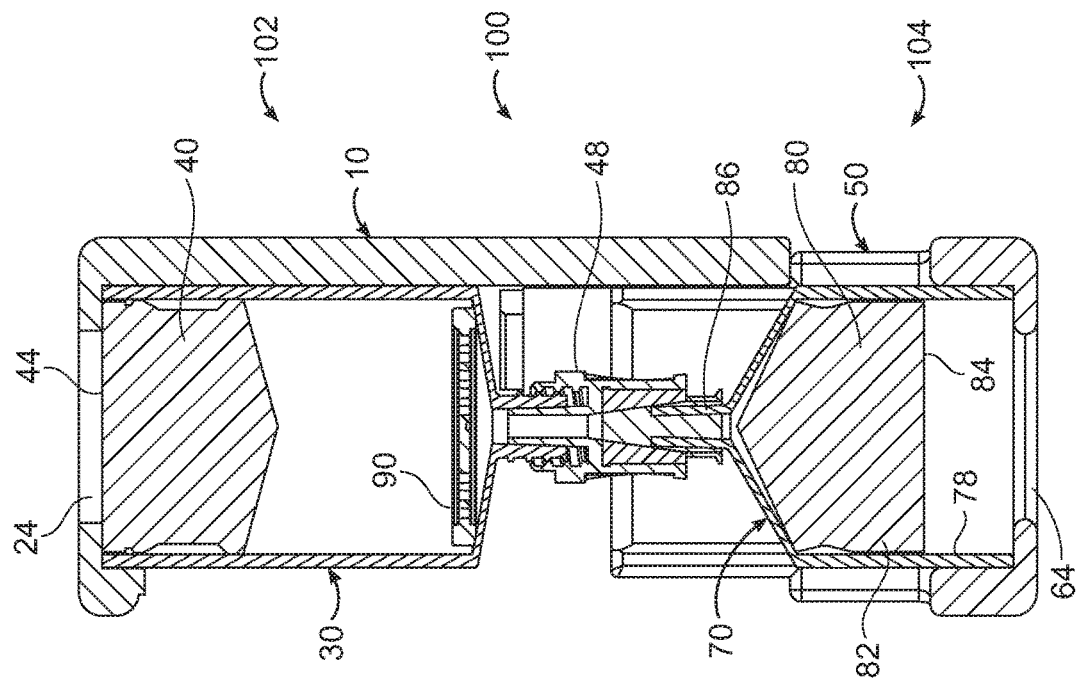
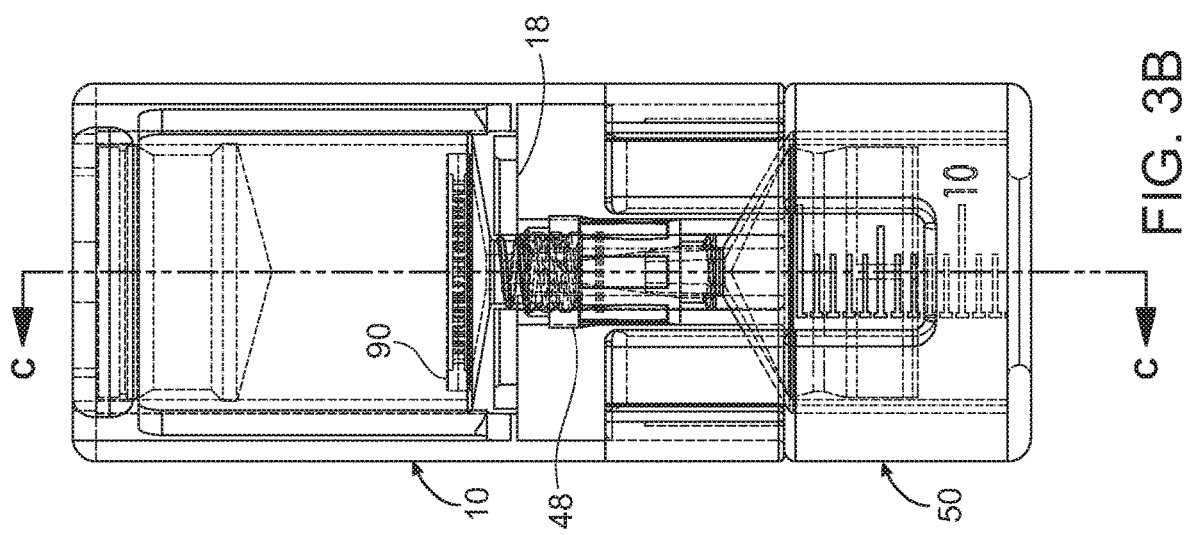

500

| Place a first volume of a physiological fluid in a first chamber of a first assembly. | — 505 |

| Place a second volume of the physiological fluid in a second chamber of a second assembly. | — 510 |

| Connect the first and second assemblies such that the first and second chambers are in fluid communication. | — 515 |

| Subject the physiological fluid in the connected first and second assemblies to centrifugation to collect a first fraction of the physiological fluid in the first chamber and second fraction of the physiological fluid in the second chamber. | — 520 |

| Disconnect the first and second assemblies. | — 525 |

| Connect the first assembly to a third assembly such that the first chamber is in fluid communication with a third chamber of the third assembly. | — 530 |

| Subject the first fraction in the connected first and third assemblies to centrifugation to collect a third fraction of the physiological fluid in the third chamber and a fourth fraction of the physiological fluid in the first chamber. | — 535 |

| Disconnect the second and third assemblies. | — 540 |

905 — Hold a physiological fluid in a syringe, the syringe including a tip, a base and a barrel that extends between the tip and the base, the syringe including a plunger positioned within the barrel, the plunger including a plunger seal in sealing engagement with an inside wall of the barrel

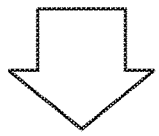

910 — Support the syringe (at least partially) within an exoskeleton, the syringe removably coupled to the exoskeleton using an interference fit.

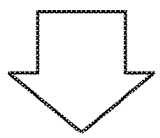

915 — Centrifuge the physiological fluid in the syringe supported by the exoskeleton.

FIG. 9

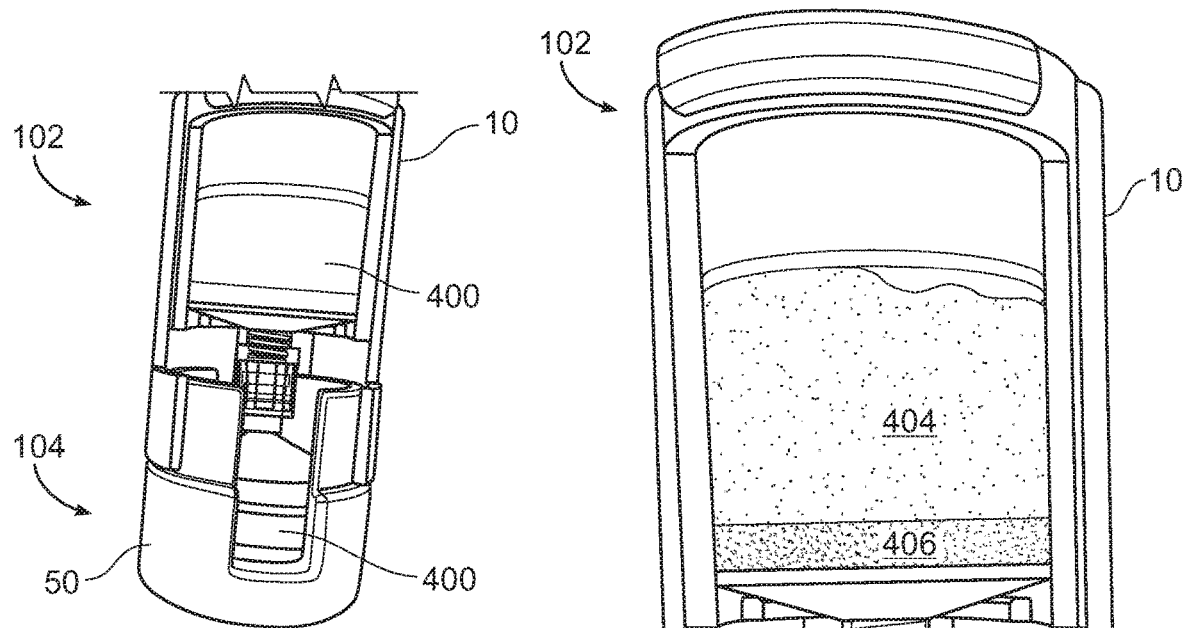
FIG. 11A
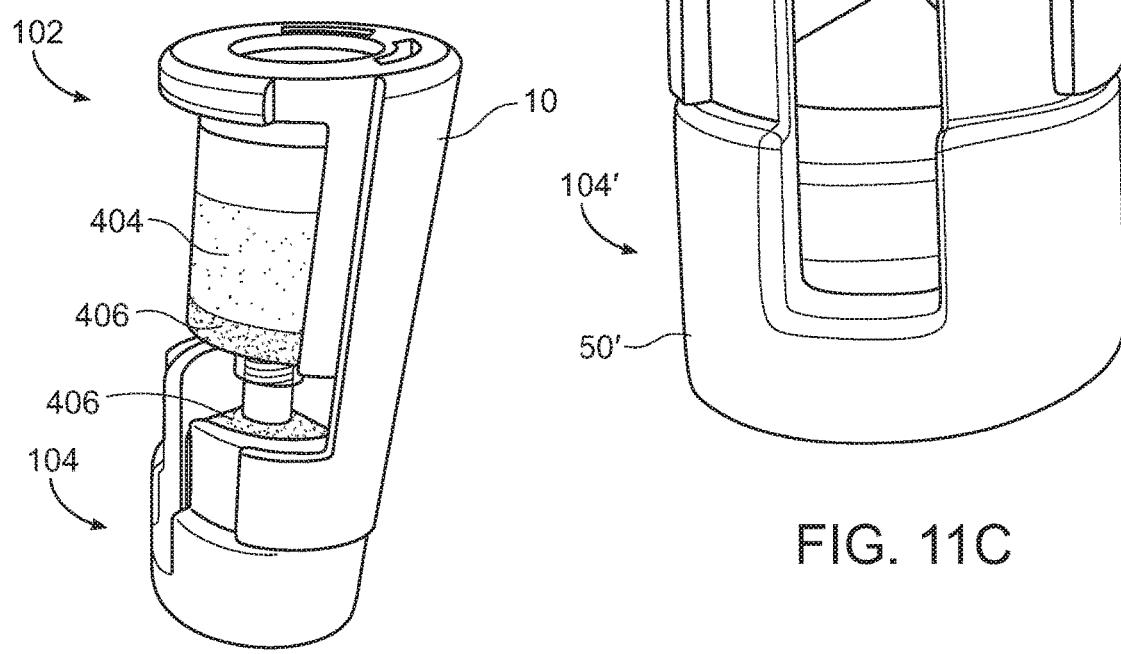
FIG. 11B
FIG. 11C

APPARATUS AND METHOD FOR CENTRIFUGING A BIOLOGIC

RELATED APPLICATION

This application is the U.S. National Stage of International Application No. PCT/US2018/063317, filed Nov. 30, 2018, which designates the U.S., published in English, and claims the benefit of U.S. Provisional Application No. 62/592,798, filed on Nov. 30, 2017. The entire teachings of the above applications are incorporated herein by reference.

BACKGROUND

Increasingly plastic surgeons are using aspirated fat, platelet rich plasma (PRP), marrow, and other biologics that are harvested at the point of care and are centrifuged to create a filler material for face-lifts and other cosmetic surgeries, such as hand and breast augmentation. The processed fat is often referred to as a fat graft procedure. The aspirated tissue is often aspirated into a syringe which is then centrifuged. Surgeons are interested in fractionating the tissue at point of care and using the various fractions to assist in the surgery or procedure. Typically, different devices are required to fractionate marrow, blood, and fat because the characteristics of the tissues are so different. For example, fat is much less dense than blood. Fat has a large amount of oil while marrow has typically little to none. Blood has a larger range of hematocrit. Fat typically has no hematocrit. Marrow has more nucleated cells than blood. Often, clinicians need to open separate kits to process fat, blood, and marrow.

Therefore, a need exists for a single system that can be used to create the different fractions of tissue that clinicians desire.

SUMMARY

Devices, systems and methods for centrifuging a physiological fluid are provided. In general, a device has at least one exoskeleton assembly including a syringe supported by an exoskeleton for use in centrifuge. A device or a system can have two exoskeleton assemblies that are connectable, each having a chamber and the two chambers in fluid communication when the assemblies are connected. Also provided is a kit having two or more pairs of exoskeleton assemblies for use in centrifuging a physiological fluid.

Centrifuging fluid in a container can cause the container to leak, deform or both. For example, typically a tube is centrifuged at between 50 and 1000 g force. A need exists to centrifuge material simply without the material leaking and to provide a means to further transfer and use the separated material. Embodiments of the present invention provide convenient and novel tools to centrifuge various tissues that are routinely aspirated during point of care procedures. These tissues typically fall under the category of adipose tissue, blood, marrow, or combinations thereof. These tissues are encompassed by the terms "biological fluid" and "physiological fluid," which are used interchangeably herein.

A device for centrifuging a physiological fluid includes a syringe including a tip, a base and a barrel extending between the tip and the base to hold a physiological fluid. The syringe includes a plunger positioned within the barrel and the plunger includes a plunger seal in sealing engagement with an inside wall of the barrel. An exoskeleton is provided to support the syringe at least partially within the exoskeleton for use in a centrifuge. The syringe is removably coupled to the exoskeleton using an interference fit.

The plunger can be without a handle attached to the plunger.

The exoskeleton can be configured to support the base and plunger of the syringe, the barrel of the syringe where the diameter of the barrel of the syringe narrows between the tip and the plunger, or both. For example, the exoskeleton can be configured to support the syringe while the g-force generated by the centrifuge is between 30 g and 3000 g.

The exoskeleton can fit tightly around a circumference of the barrel at the base of the syringe, the exoskeleton, when the syringe is subjected to elevated g-force from the centrifuge, supporting the base and plunger in a manner that prevents distortion of the syringe barrel that prevents fluid from leaking around the seal created between the inside wall of the barrel and the plunger seal.

The exoskeleton can support a portion of the barrel of the syringe where the diameter of the barrel of the syringe narrows between the tip and the plunger so that, when the syringe is subjected to elevated g-force from a centrifuge, the force of the centrifuge is absorbed by the exoskeleton and barrel of the syringe and not the tip of the syringe.

The exoskeleton can be tube-shaped and can define a central lumen for receiving the syringe.

The exoskeleton can have a sidewall with a longitudinal opening to facilitate one or more of viewing the syringe, accessing the syringe, and loading and unloading the syringe into and from the exoskeleton.

The height of the lumen of the exoskeleton can be greater than the height of the syringe measured from the syringe base to the syringe tip so that when the syringe is assembled into the exoskeleton at least one longitudinal section of the syringe is fully encompassed within the exoskeleton.

The syringe tip can be capped and the exoskeleton can have a closed bottom to support the capped tip of the syringe and an open top to receive the barrel of the syringe.

The tube-shaped exoskeleton can comprise two parts that can be assembled onto the syringe, one part configured to support the barrel of the syringe and the other part configured to support the tip of the syringe.

The exoskeleton can have a stop facing inwardly to support at least a portion of the barrel of the syringe near the tip where the diameter of the barrel is tapered. The stop can be formed by one or more ridges, lips, shelves etc., which can be positioned at the appropriate height and protrude into the lumen of the exoskeleton.

The device can comprise two exoskeletons and two syringes, each exoskeleton supporting a syringe, wherein the two syringes and exoskeletons can be assembled to a single structure with the syringes connected by a Luer to Luer connection. The Luer to Luer connection can include a female swabable Luer at one of the syringes and a male slip fit Luer at the other of the syringes. One of the exoskeletons can include a stop and the assembled exoskeletons can create an interference fit that absorbs the force created by the centrifuge, the stop and the interference fit preventing the Luer to Luer connection from breaking during centrifugation. The two syringes can be in fluid communication when assembled as a single structure.

The exoskeleton can include a base having a hole to provide access to the plunger of the syringe.

The device can further include a screen in the syringe between the plunger and the tip of the syringe. The screen can have a circumference such that it creates a press fit between the inside wall of the barrel and the screen when inserted into the syringe.

A device for centrifuging a physiological fluid includes a first syringe including a Luer tip, a base and a barrel extending between the tip and the base to hold a first volume of a physiological fluid. The first syringe includes a plunger positioned within the barrel and in sealing engagement with an inside wall of the barrel. A first exoskeleton is provided to support a circumference of the barrel at the base of the first syringe so that the first syringe, when subjected to elevated g-force from a centrifuge, is supported by the first exoskeleton that prevents distortion of the barrel that prevents fluid from leaking around the sealing engagement between the inside wall of the barrel and the plunger of the first syringe, the first exoskeleton including a stop facing inwardly to support a portion of the barrel where the diameter of the barrel of the first syringe narrows between the Luer tip and the plunger. The device further includes a second syringe including a Luer tip, a base and a barrel extending between the tip and the base to hold a second volume of the physiological fluid. The second syringe includes a plunger positioned within the barrel and in sealing engagement with an inside wall of the barrel. A second exoskeleton is provided to support a circumference of the barrel at the base of the second syringe so that the second syringe, when subjected to elevated g-force from the centrifuge, is supported by the second exoskeleton that prevents distortion of the barrel that prevents fluid from leaking around the sealing engagement between the inside wall of the barrel and the plunger of the second syringe. The first and second syringes and the first and second exoskeletons can be assembled into a single structure with the syringes connected by a Luer to Luer connection.

A method for centrifuging a physiological fluid includes holding a physiological fluid in a syringe, the syringe including a tip, a base and a barrel extending between the tip and the base, the syringe including a plunger positioned within the barrel, the plunger including a plunger seal in sealing engagement with an inside wall of the barrel; supporting the syringe at least partially within an exoskeleton, the syringe being removably coupled to the exoskeleton using an interference fit; and centrifuging the physiological fluid in the syringe supported by the exoskeleton.

The physiological fluid can be centrifuged with the base of the syringe away from a center of a centrifuge rotor or with the tip of the syringe away from a center of a centrifuge rotor.

A system for centrifuging a physiological fluid includes a first exoskeleton assembly including a first syringe supported by a first exoskeleton, the first syringe having a first chamber to hold a first volume of a physiological fluid. The system includes a second exoskeleton assembly including a second syringe supported by a second exoskeleton, the second syringe having a second chamber to hold a second volume of a physiological fluid, the first volume being larger than the second volume, the first and second exoskeleton assemblies connectable such that the first and second chambers are in fluid communication. The physiological fluid in the connected first and second exoskeleton assemblies can be subjected to centrifugation to collect a first fraction of the physiological fluid in the first chamber and second fraction of the physiological fluid in the second chamber.

The system can further include a collection syringe to couple to the second syringe to remove the second fraction from the second chamber after centrifugation.

The system can further include a third exoskeleton assembly including a third syringe supported by a third exoskeleton, the third syringe having a third chamber, the third exoskeleton assembly connectable to the first exoskeleton assembly when the first and second exoskeleton assemblies are disconnected, such that the first chamber is in fluid communication with the third chamber, wherein the first fraction in the connected first and third exoskeleton assemblies can be subjected to centrifugation to collect a third fraction of the physiological fluid in the third chamber and a fourth fraction of the physiological fluid in the first chamber.

The system can further include a collection syringe to couple to the third syringe to remove the third fraction from the third chamber after centrifugation.

The system can further include a collection syringe to couple to the first syringe to remove the fourth fraction from the first chamber after centrifugation.

In an embodiment, the physiological fluid is bone marrow aspirate, the first fraction includes platelets, white blood cells and plasma, the second fraction includes primarily red blood cells, the third fraction includes platelet rich plasma and white blood cells, and the fourth fraction includes primarily platelet poor plasma.

The first and second chamber can be configured such that the first volume is about three times larger than the second volume. The 3:1 volume ratio (e.g. 15 cc/5 cc) has been found to be useful for isolating and extracting target fluid fractions. Selection of this ratio considers average hematocrit of patients. When processing blood or marrow aspirate using this volume ratio, the target tissue (e.g., buffy coat) is in a top chamber after the first centrifugation step and in a bottom chamber after the second centrifugation step.

The connected first and second exoskeleton assemblies can include the first and second syringes connected using a Luer to Luer connection, and can include the first and second exoskeletons connected using an interference fit.

A method for centrifuging a physiological fluid includes placing a first volume of a physiological fluid in a first chamber of a first syringe supported by a first exoskeleton, the first syringe and first exoskeleton comprising a first exoskeleton assembly; placing a second volume of the physiological fluid in a second chamber of a second syringe supported by a second exoskeleton, the first volume being larger than the second volume, the second syringe and second exoskeleton comprising a second exoskeleton assembly; connecting the first and second exoskeleton assemblies such that the first and second chambers are in fluid communication; subjecting the physiological fluid in the connected first and second exoskeleton assemblies to centrifugation to collect a first fraction of the physiological fluid in the first chamber and second fraction of the physiological fluid in the second chamber; and disconnecting the first and second exoskeleton assemblies.

The method can further include removing the second fraction from the second chamber after centrifugation.

Further, the first exoskeleton assembly can be connected to a third exoskeleton assembly such that the first chamber is in fluid communication with a third chamber of a third syringe supported by a third exoskeleton, the third syringe and third exoskeleton comprising the third exoskeleton assembly. The first fraction in the connected first and third exoskeleton assemblies can be subjected to centrifugation to collect a third fraction of the physiological fluid in the third chamber and a fourth fraction of the physiological fluid in the first chamber. After centrifugation, the second and third exoskeleton assemblies can be disconnected.

The method can further include removing the third fraction from the third chamber after centrifugation, and optionally removing the fourth fraction from the first chamber after centrifugation.

A kit for centrifuging a biological fluid includes a pair of first exoskeleton assemblies, a pair of second exoskeleton assemblies and a pair of third exoskeleton assemblies. Each first exoskeleton assembly includes a first syringe supported by a first exoskeleton, the first syringe having a first chamber to hold a first volume of a physiological fluid. Each second exoskeleton assembly includes a second syringe supported by a second exoskeleton, the second syringe having a second chamber to hold a second volume of a physiological fluid, the first volume being larger than the second volume. The first and second exoskeleton assemblies are connectable such that the first and second chambers are in fluid communication. In some embodiments, each second exoskeleton assembly is simply a second exoskeleton (e.g., a bottom support to couple to the first exoskeleton) and does not include the second syringe. Each third exoskeleton assembly includes a third syringe supported by a third exoskeleton, the third syringe having a third chamber. The third exoskeleton assembly is connectable to the first exoskeleton assembly when the first and second exoskeleton assemblies are disconnected, such that the first chamber is in fluid communication with the third chamber.

The kit can further include one or more collection syringes. A first collection syringe can be provided to couple to the first syringe to remove the fourth fraction from the first chamber after centrifugation, a second collection syringe can be provided to couple to the second syringe to remove the second fraction from the second chamber after centrifugation, and a third collection syringe can be provided to couple to the third syringe to remove the third fraction from the third chamber after centrifugation.

A method for centrifuging a physiological fluid includes placing a first volume of a physiological fluid in a first chamber of a first assembly; placing a second volume of the physiological fluid in a second chamber of a second assembly; connecting the first and assemblies such that the first and second chambers are in fluid communication; subjecting the physiological fluid in the connected first and second assemblies to centrifugation to collect a first fraction of the physiological fluid in the first chamber and second fraction of the physiological fluid in the second chamber; and disconnecting the first and second assemblies.

The method can further include connecting the first assembly to a third assembly such that the first chamber is in fluid communication with a third chamber of the third assembly; subjecting the first fraction in the connected first and third assemblies to centrifugation to collect a third fraction of the physiological fluid in the third chamber and a fourth fraction of the physiological fluid in the first chamber; and disconnecting the second and third assemblies.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 1D is a side view of the exoskeleton assembly of FIG. 1C illustrating a screen in the syringe supported by the exoskeleton FIG. 1E is a sectional view of the exoskeleton assembly of FIG. 1D.

FIG. 3B is a side view of the two tube shaped exoskeletons and syringes assembled with the upper and lower exoskeletons each supporting a syringe with the syringes connected and in fluid communication through the Luer connection and the exoskeletons connected through a keyway mating feature.

FIG. 3C is a sectional view of connected upper and lower exoskeletons assemblies of FIG. 3B.

FIG. 5 is a flow diagram of a method for centrifuging a physiological fluid according to an example embodiment of the invention.

FIG. 9 is a flow diagram of another method for centrifuging a physiological fluid according to an example embodiment.

FIG. 11A is a perspective view of an example device including upper and lower exoskeleton assemblies. Each assembly includes a syringe supported by an exoskeleton. Upper and lower syringes are both loaded with marrow, and are connected and in fluid communication via Luer fittings, prior to a first centrifugation step.

FIG. 11B is a perspective view of the connected assemblies of FIG. 11A after the first centrifuge step. In the lower chamber are red blood cells and in the upper assembly are red blood cells on the bottom and on top of that cloudy yellow plasma.

FIG. 11C is a perspective view of the device after the first centrifugation step and after the first lower assembly containing primarily red cells has been removed and replaced by an identical, empty assembly. This empty lower assembly is connected to the upper assembly with the syringes being in fluid communication. This entire structure is then placed back into the centrifuge.

DETAILED DESCRIPTION

Figure 1A:
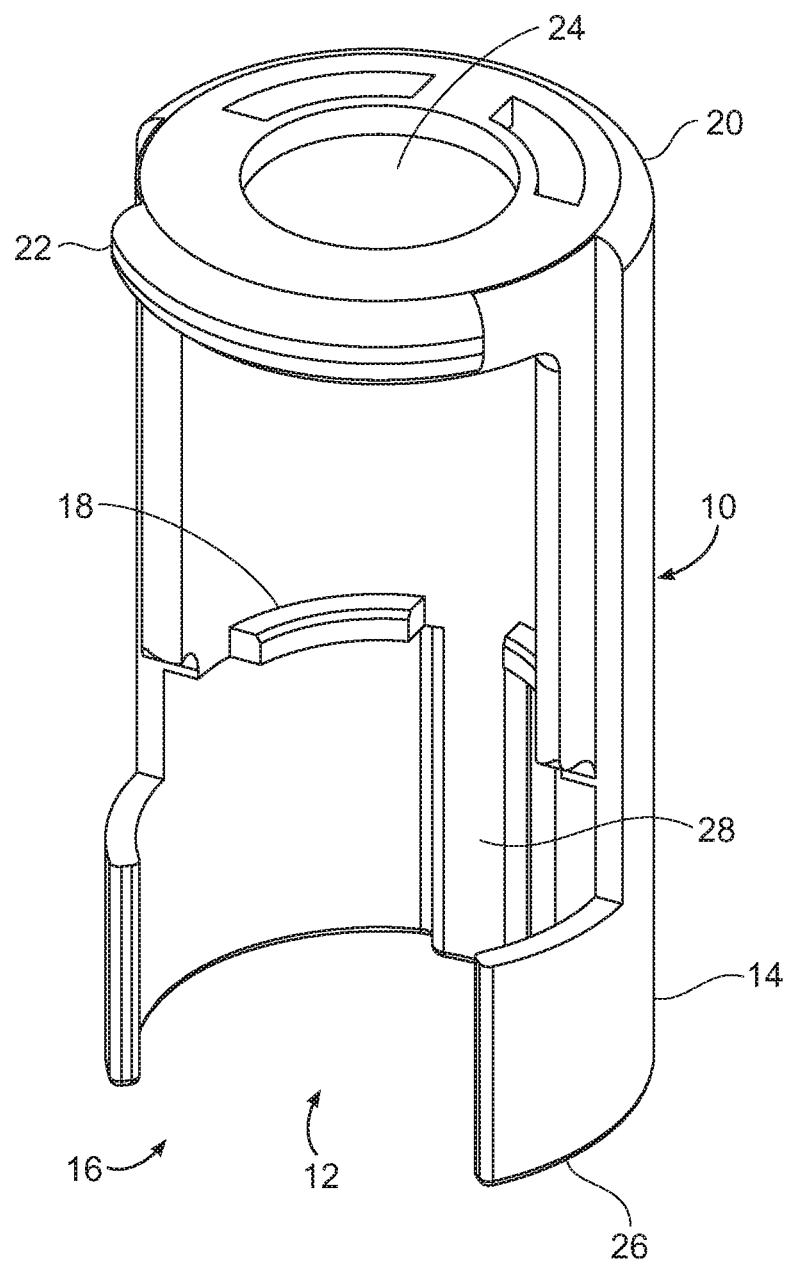
FIG. 1A is a perspective view of an exoskeleton according to an example embodiment.

A description of example embodiments follows.

Embodiments of the present invention provide exoskeletons to support syringes for use in a centrifuge. The syringes typically do not have a handle attached to the syringe plunger and can be assembled and dis-assembled from their supporting exoskeleton. An exoskeleton and syringe when assembled, can be joined to a different exoskeleton and syringe that is also assembled. When an exoskeleton and syringe assembly is then connected to another exoskeleton and syringe assembly, the syringes can be sized to hold different amounts of fluid by using different sized syringes or syringes that hold different volumes of fluid. When centrifuged in this combination, the two syringes, e.g., one upper syringe in an upper exoskeleton and one lower syringe in a lower exoskeleton, are in fluid communication with each other through a Luer connection. The upper and lower the syringes supported by respective upper and lower exoskeletons can be attached and de-attached through a Luer connection.

Various combinations of fractionated biologics using a centrifuge can be created with the apparatus described when used alone or in combination. A useful feature of the devices is that the exoskeleton containing the syringe can be centrifuged in multiple orientations with the exoskeleton preventing the Luer tip of the syringe from breaking or the exoskeleton preventing fluid leak around the barrel of the syringe. The components in the syringes in the exoskeletons can be centrifuged individually or in combination and in various orientations and combinations.

In an embodiment, the present invention provides an exoskeleton that supports a standard syringe that has had its length shortened by removing a portion of the plunger and/or barrel of the syringe. The exoskeleton is meant to support the syringe to keep it from breaking or leaking when in the centrifuge. The exoskeleton therefore needs to at least support the part of the syringe that is distal to the center of the rotor of the centrifuge. By selectively shortening the syringe to fit into the exoskeleton, different volumes of material can be selected to fill the syringe. The shape of the exoskeleton can be selected to fully support the Luer tip or plunger in the barrel of the syringe during centrifugation. For example, A) the exoskeleton support can prevent fluid leak around the plunger of the syringe when the plunger of the syringe is placed in an orientation distal to the center rotor of the centrifuge such that the force created by the centrifuge is primarily toward the plunger or B) the exoskeleton can support the Luer tip to prevent breaking when the syringe is placed in a centrifuges with the Luer tip in an orientation distal to the center rotor of the centrifuge such that the force created by the centrifuge is primarily towards the Luer tip.

In an embodiment, the exoskeleton for the single syringe can be tube-shaped or can be a tube. The tube can be open on both ends, closed on both ends, or closed on one end only. If the tube is open on both ends, the modified syringe can be placed into a tube from either end (e.g., by sliding the syringe into a tube). The tube has a length that substantially encompasses the syringe in a snug manner. When the tube is open on both ends, the syringe with the cut handle can be loaded into the tube so that the finger wings of the syringe are against the outside of the tube. The tube and syringe can be placed in a centrifuge bucket. The tube and syringe can be placed in a centrifuge bucket such that the plunger end of the syringe in the tube is down and the Luer tip is up so that the Luer tip is near the opening of the tube nearest the center of the rotor and distal to the greatest force created by the centrifuge so that the denser material in the syringe is collected on the plunger in the barrel distal to the Luer tip. In one orientation, the bottom of the bucket, combined with the force of the tube pressing against the finger wings of the syringe prevents the plunger and syringe from separating during centrifugation which would cause a fluid to leak. The tube can have a closed bottom. If the tube has a closed bottom the syringe is loaded from one direction into the tube. For example, the tube can be closed and the diameter of the tube can be sized to create a modest press fit around the barrel and plunger. The tube can be cut with each half having at least one end open. The exoskeleton tube can be fitted (tube slid over the cut syringe) from each end of the syringe. The tube can be in the shape of a clam shell with a nest that fits the cut syringe, two halves, with the syringe placed into a first half and then the second half fits over the first half.

A useful and advantageous feature of embodiments described is that the syringe can be centrifuged in two different orientations, plunger down or Luer tip down, and still have the syringe supported at the point distal to the center of the rotor by at least one exoskeleton. Two different exoskeletons can be used depending on which end of the syringe is facing distal to the center of the rotor. The exoskeletons support at least the tip of the syringe or the plunger of the syringe. For example, A) the exoskeleton supports around the exterior circumference of the barrel at the base of the syringe distal to the Luer tip when positioned in the centrifuge in one orientation or B) the Luer tip is supported by an exoskeleton at a location exterior to the barrel of the syringe where the diameter of the barrel of the syringe narrows proximal to the Luer fitting and distal to the plunger when positioned in the centrifuge in an opposite orientation. A useful and advantageous feature for centrifuging with the Luer tip facing distal to the center of the rotor is that the g force can be absorbed by the exoskeleton and the barrel of the syringe, sparing having all the force on a single narrow point like the Luer tip. If all the force was against an unsupported Luer tip, a risk exists that the Luer tip would break. Also, the tolerance can be made that some pressure to a certain distance can be applied to a Luer cap on the end of the syringe, preferably a slip fit syringe. This pressure, arising from the force of the centrifuge, will cause the cap to press tighter against the syringe preventing leaking, but after a certain level of tightening, the cap cannot go further onto the slip fit because of the interference from the barrel of the syringe and the exoskeleton.

The device can be set up so that two different exoskeletons and syringes are provided that can be separated and joined in an easy manner. When joined, the two syringes are in fluid communication with each other. The syringes supported by the two-piece exoskeleton can be centrifuged in either orientation and the syringes can be connected by a Luer to Luer connection at the center. Thus, the combined exoskeleton and syringe assemblies can each be selectively separated from each other, and each syringe can be selectively separated from the respective exoskeleton. Fluid is forced from one syringe to the other when assembled and centrifuged in this manner. The volume of fluid held in the upper and lower syringes can be different by using different size syringes and by either cutting the plunger of the syringe such that it can only go back a pre-determined distance within the exoskeleton before hitting the support structure and/or by making the size of the chambers within the support structure different.

A useful feature of the exoskeleton beyond supporting the modified syringe during centrifugation is that that support structure prevents the plunger of the syringe from going out the back resulting in a fluid leak if more than the maximum fill is attempted to be loaded into the syringe.

A screen made of a dense material such as steel can be placed in a single syringe or in either or both syringes that are assembled into the two-piece exoskeleton. When the syringe with the screen is in the upper syringe in the two-piece exoskeleton configuration and during centrifugation, the fluid in the upper syringe is forced over the screen before entering the lower syringe.

A closed cell sponge and open cell sponge combination can be placed inside the syringe. The combination of a piece of open cell sponge and a piece of closed cell sponge can cause the two pieces to be less dense than any fluid in the syringe. The combination of the two pieces when placed inside of a syringe can be orientated so that the closed cell foam pushes up the open cell foam when placed in a fluid. This can be accomplished by placing first the closed cell foam into the barrel of the syringe closest to the Luer tip, followed by the open cell foam and then placing the plunger behind that. The syringe can be centrifuged Luer tip down so that the greatest force is against the Luer tip and the densest material is opposite to the plunger. After centrifugation, the open cell sponge always floats to the top of the syringe. The open cell sponge material can be hydrophilic and absorb fluid. Air can be evacuated from the syringe containing the sponges before centrifugation such that after centrifugation, the sponges are always immersed in fluid. The sponges can be compressed during loading to minimize air that is loaded into the syringe. The sponge material or sponges can work to supplement the screen or can be used in place of a screen.

A further useful feature of the system is that if the syringe in the assembly is not filled to the max, under-filling is not a problem. No matter how much the syringe is filled with fluid, once the centrifugation starts, the g force from the centrifuge forces the plunger to the bottom of the barrel and into the clip (exoskeleton) support ring. During centrifugation, the densest material (often in a biologic material, cells are the densest material) is captured on top of the plunger in the base of the syringe. When the centrifuge slows down, the plunger returns to its normal level in the barrel but none of the fractionated material (e.g., cells) re-mixes. This is similar to when one caps a syringe and pulls the plunger all the way back; when one lets go of the plunger, it goes back to its previous location in the barrel.

Advantageously, when the plunger is fully extended in the barrel, whether because the syringe has been fully loaded or, if the syringe has only been partially filled, the force of the centrifuge is driving the plunger to the bottom of the barrel during centrifugation, the plunger rests in the base of the exoskeleton that supports it when the assembly is under force.

Embodiments of the invention can include Luer fittings and/or use Luer to Luer connection(s) to achieve fluid communication between components. The Luer taper is a standardized system of small-scale fluid fittings (connectors) used for making leak-free connections between a male-taper fitting (connector) and its mating female part on medical and laboratory instruments, including syringe tips and needles.

FIGS. 1A-1E illustrate a device for centrifuging a biological fluid according to an example embodiment. The device includes an exoskeleton 10 configured to receive and support a syringe 30.

Figure 1B:
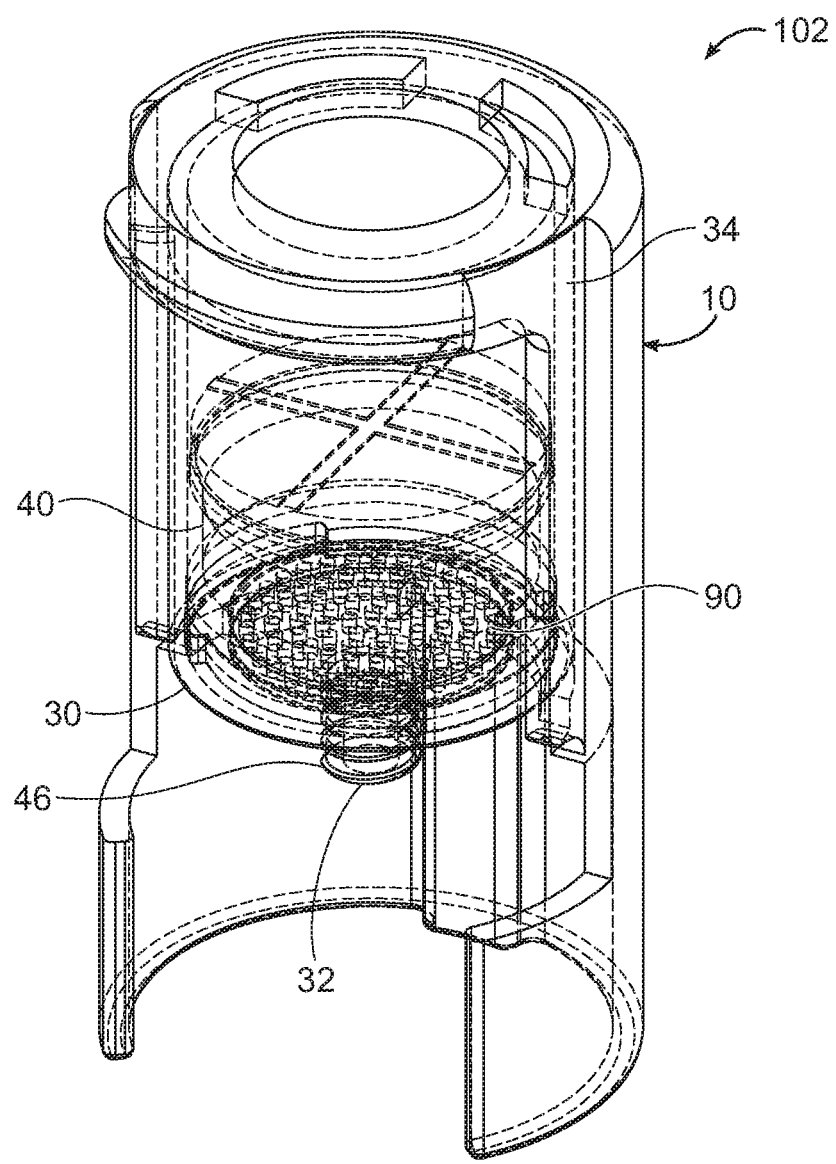
FIG. 1B is a perspective view of an exoskeleton assembly including the exoskeleton of FIG. 1A holding a syringe with the proximal and distal ends of the syringe supported by the exoskeleton.
Figure 1C:
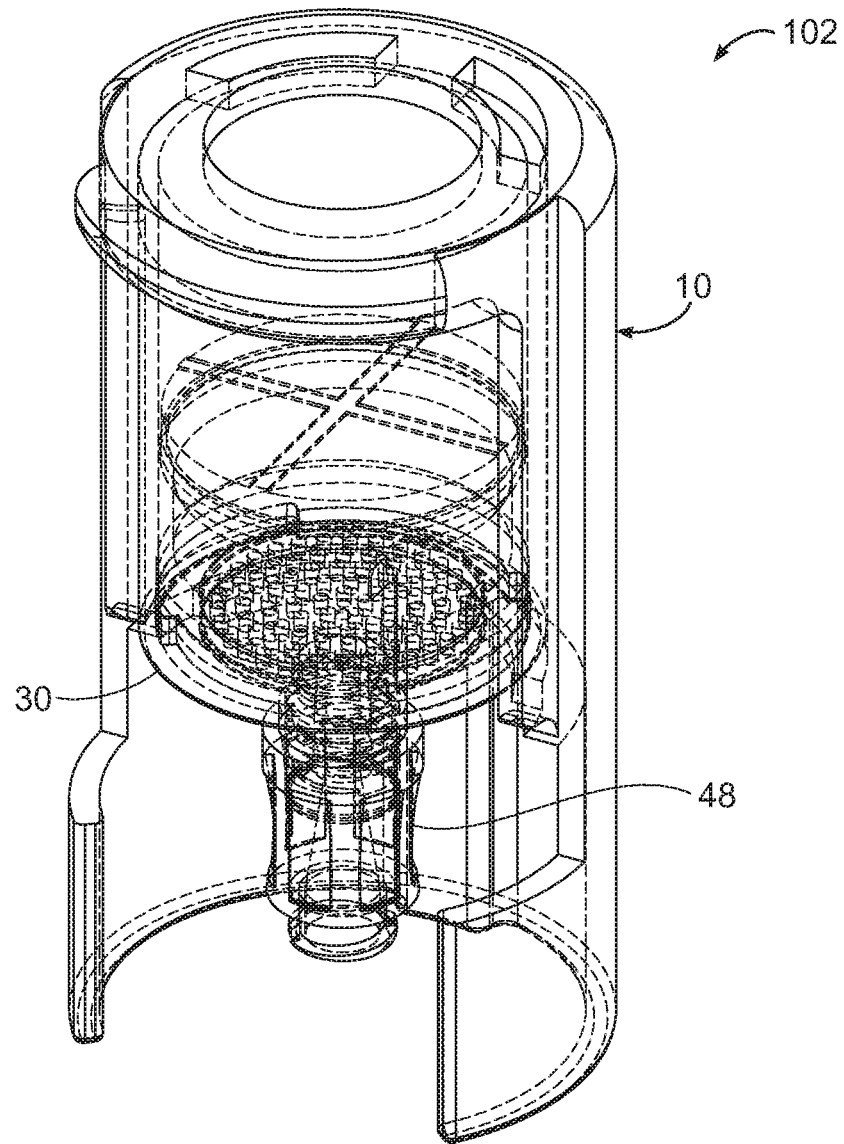
FIG. 1C is a perspective view of the exoskeleton assembly of FIG. 1B with a Luer fitting attached to the tip of the syringe.

FIG. 1A is a perspective view of exoskeleton 10 defining a lumen 12 to receive syringe 30. The syringe 30 can be coupled to the exoskeleton 10, as illustrated in FIG. 1B, to form an exoskeleton assembly 102. The exoskeleton 10 holds syringe 30 with both the proximal end of the syringe (e.g., at base 34) and distal end of the syringe (e.g., at tip 32) supported by the exoskeleton 10. A Luer fitting 48 can be attached to a threaded female Luer connector 46 at the tip 32 of the syringe of the exoskeleton assembly, as illustrated in FIG. 1C.

FIGS. 1D and 1E are side and sectional views, respectively, of the exoskeleton assembly 102 illustrating various features of the exoskeleton 10 and syringe 30, including a screen 90 in the syringe. Features of screen 90 are described with reference to FIG. 4.

As best seen in FIG. 1E, the syringe 30 includes tip 32, base 34 and a barrel 36 extending between the tip and the base to hold a physiological fluid. The syringe includes a plunger 40 positioned within the barrel 36 and the plunger includes a plunger seal 42 in sealing engagement with an inside wall 38 of the barrel. The exoskeleton 10 supports the syringe 30 at least partially within the exoskeleton for use in a centrifuge. The syringe 30 is removably coupled to the exoskeleton 10 using an interference fit. In the embodiment shown, the exoskeleton 10 is tube-shaped and defines a central, tube-shaped lumen 12 for receiving the syringe 30. The outside of the exoskeleton 10, however, need not be tube-shaped. Parts, such as the base, may be rectangular to fit a particular centrifuge. To provide an interference fit, the exoskeleton 10 can be configured such that the inner diameter of the exoskeleton is basically the same as the outer diameter of the syringe 30. Ideally, there is no space between the outer wall of the syringe and the inner wall of the exoskeleton.

The plunger 40 does not have a handle attached to the plunger. The exoskeleton 10 includes a base support 22 having a hole 24 to provide access to the plunger 40 of the syringe. The hole is sized so that the back 44 of the plunger 40 cannot pass. This prevents the plunger 40 from being pushed out of the syringe 30 during loading with fluid and/or during centrifugation.

The exoskeleton 10 can be configured to support the base 34 and plunger 40 of the syringe, to support the barrel 36 of the syringe where the diameter of the barrel of the syringe narrows between the tip and the plunger, or both as is the case in the embodiment shown in FIGS. 1A-1E.

The exoskeleton can be configured to support the syringe while the g-force generated by the centrifuge is between 30 g and 3000 g. The exoskeleton is manufactured from materials suitable for supporting a syringe during centrifugation. For example, the exoskeleton can be manufactured from a durable plastic polymer, such as acrylonitrile butadiene styrene (ABS). Syringes as commonly manufactured from the thermoplastic polymer polypropylene (PP).

The exoskeleton 10 can fit tightly around a circumference of the barrel 36 at the base 34 of the syringe, the exoskeleton, when the syringe is subjected to elevated g-force from the centrifuge, supporting the base and plunger in a manner that prevents distortion of the syringe barrel 36 that prevents fluid from leaking around the seal created between the inside wall 38 of the barrel and the plunger seal 42.

The exoskeleton 10 can support a portion of the barrel 36 of the syringe where the diameter of the barrel narrows between the tip 32 and the plunger 40 so that, when the syringe is subjected to elevated g-force from a centrifuge, the force of the centrifuge is absorbed by the exoskeleton 10 and the barrel 36 of the syringe and not the tip 32 of the syringe.

The exoskeleton 10 has a top end 20, a bottom end 26, and extending therebetween a sidewall 14 with a longitudinal opening 16 (FIG. 1A) to facilitate viewing the syringe, accessing the syringe, and loading and unloading the syringe into and from the exoskeleton 10. The opening 16 is size to allow the exoskeleton 10 to snap fit around the barrel of the syringe 30. This, in combination with the stop feature provided by one or more inwardly protruding ridges 18, can lock the syringe 30 in place, thereby preventing movement of the syringe once assembled into the exoskeleton 10.

As shown in FIGS. 1A, 1D, and 1E, the exoskeleton 10 has a stop formed by two ridges 18 facing inwardly to support a portion of the barrel 36 of the syringe near the tip 32 where the diameter of the barrel is tapered.

The height of the lumen 12 of the exoskeleton 10 can be greater than the height of the syringe 30 measured from the syringe base 34 to the syringe tip 32 so that when the syringe is assembled into the exoskeleton at least one longitudinal section of the syringe is fully encompassed within the exoskeleton.

In some embodiments, the exoskeleton comprises two parts that can be assembled onto the syringe, one part configured to support the barrel of the syringe and the other part configured to support the tip of the syringe.

Figure 2A:
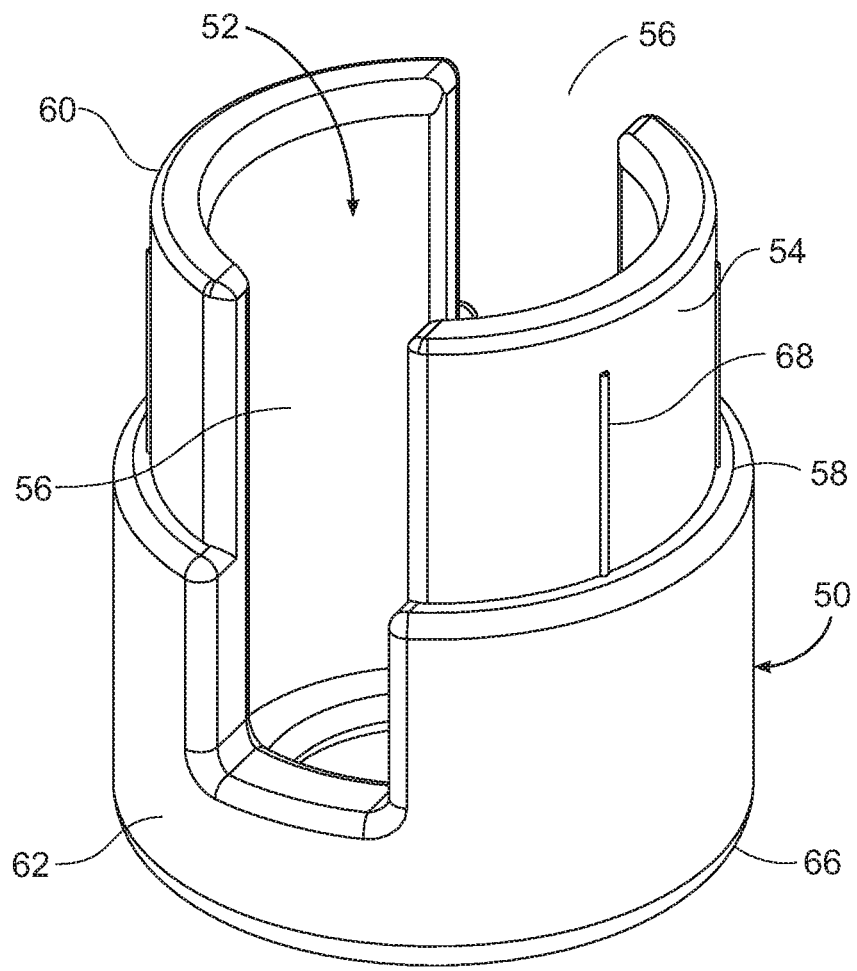
FIG. 2A is a perspective view of a tube-shaped exoskeleton to hold a syringe.
Figure 2B:
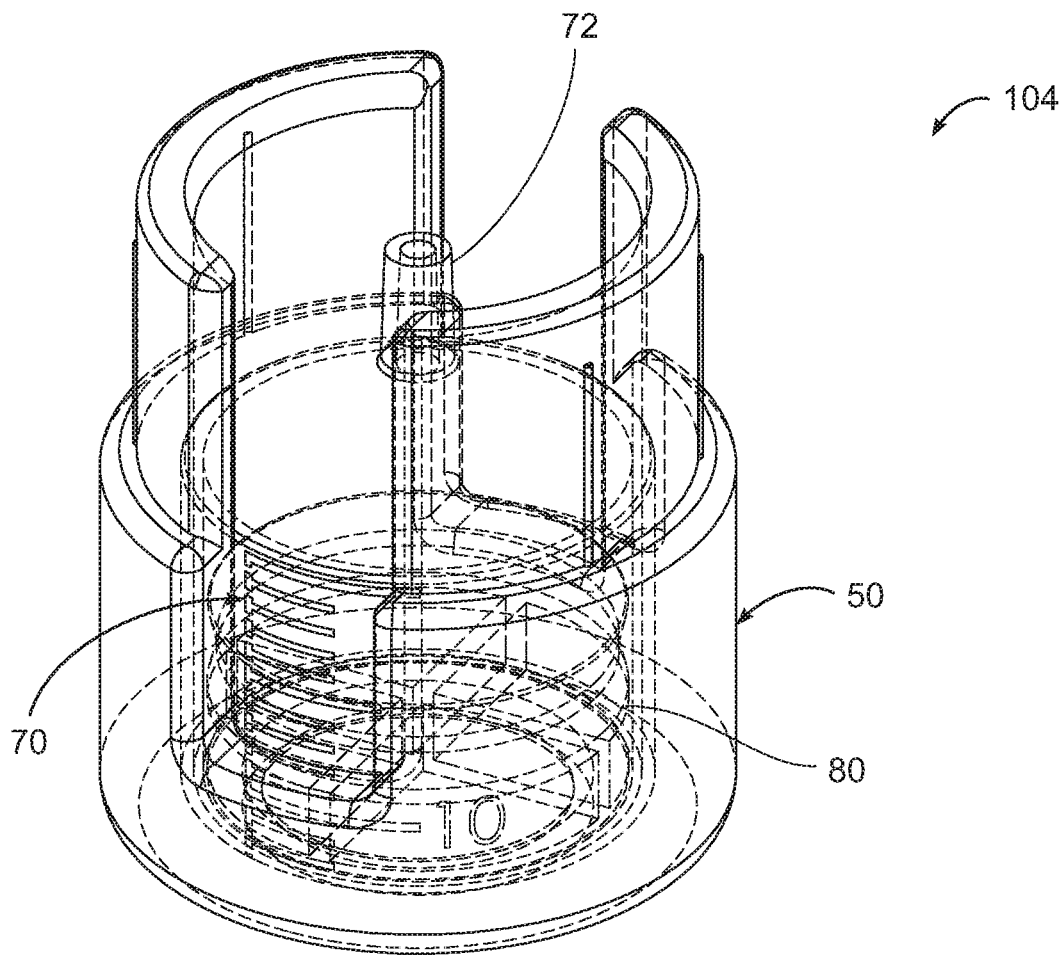
FIG. 2B is a perspective view of the exoskeleton of FIG. 2A holding a syringe. The barrel of the syringe with the end distal to the Luer tip is tightly and fully encompassed and supported around the circumference by the exoskeleton. This support covers the barrel substantially around the plunger when the plunger is at its furthest distance into the barrel of the syringe.
Figure 2C:
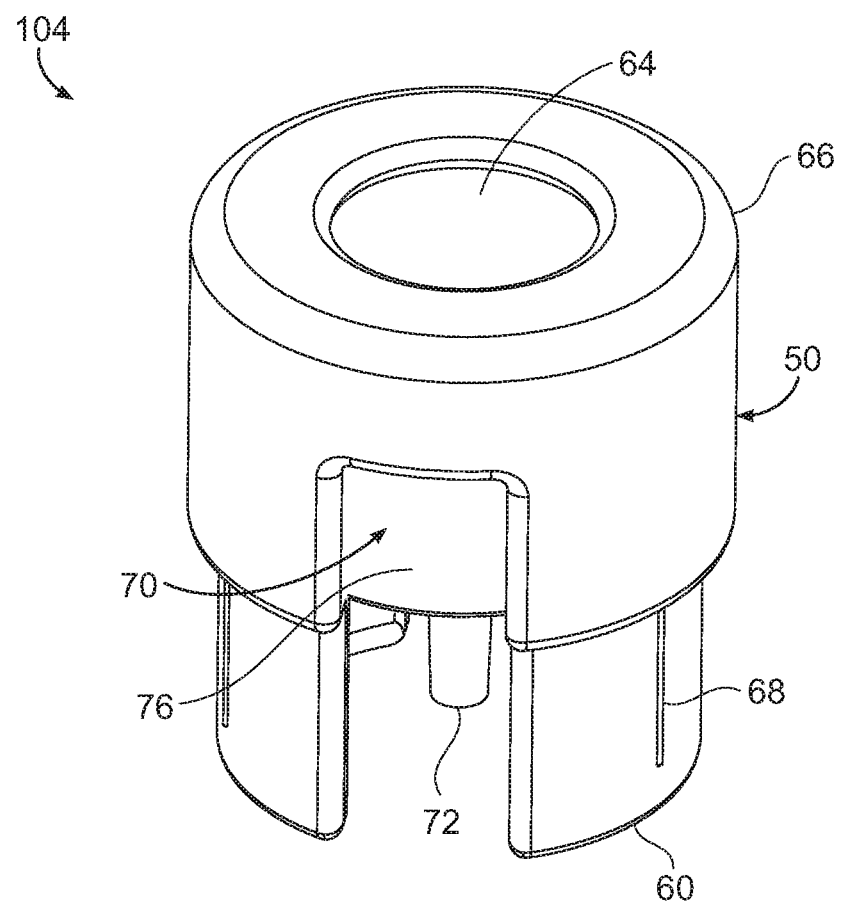
FIG. 2C is a bottom perspective view of the exoskeleton and syringe of FIG. 2B.

FIGS. 2A-2C illustrate an example exoskeleton assembly 104 that can be used as a standalone device to centrifuge a biological fluid or can be used in combination with the exoskeleton 102 assembly of FIGS. 1A-1E.

FIG. 2A is a perspective view of a tube-shaped exoskeleton 50 to hold a syringe. The exoskeleton includes a sidewall 54 and defines a central lumen 52 for receiving the syringe through the open top end 60. The sidewall 54 includes two longitudinal openings 56 to facilitate viewing the syringe, accessing the syringe, and loading and unloading the syringe into and from the exoskeleton 50.

In some embodiments, the height of the lumen 52 of the exoskeleton 50 (e.g., from top end 60 to bottom end 66) is configured be greater than the height of the syringe, measured from a syringe base to a syringe tip, so that when the syringe is assembled into the exoskeleton at least one longitudinal section of the syringe is fully encompassed within the exoskeleton, as illustrated in FIG. 2B.

FIG. 2B and FIG. 2C are top and bottom is a perspective views of the exoskeleton 50 of FIG. 2A holding a syringe 70 and forming exoskeleton assembly 104. The syringe includes a tip 72, a base 74, and a barrel 76. Within the barrel 76 is a plunger 80. The barrel of the syringe, with the end distal to the Luer tip, is tightly and fully encompassed and supported around its circumference by the exoskeleton 50. This support covers the barrel 76 substantially around the plunger 80 when the plunger is at its furthest distance into the barrel of the syringe, such as during centrifugation. The plunger 80 is slidably positioned in the syringe 70 and includes a plunger seal 82 to sealingly engage an inside wall 78 of the syringe 70 (see, e.g., FIG. 3C). A base support 62 at the bottom end 66 of exoskeleton 50 prevents the plunger 80 from sliding out of the syringe 70, such as during centrifugation. This feature is also useful during loading of fluid into the syringe 70. A hole 64 at the bottom end 66 of the exoskeleton 50 provides access to the syringe and plunger. The hole is sized to prevent the plunger 80 from falling out of the syringe, when the syringe is supported by the exoskeleton 50. The back 84 of the plunger 80 will not pass through the hole 64 (see, e.g., FIG. 3C).

The device can comprise two exoskeletons and two syringes, each exoskeleton supporting a syringe, wherein the two syringes and exoskeletons can be assembled to a single structure with the syringes connected by a Luer to Luer connection. This is illustrated in FIGS. 3A-3C.

Figure 3A:
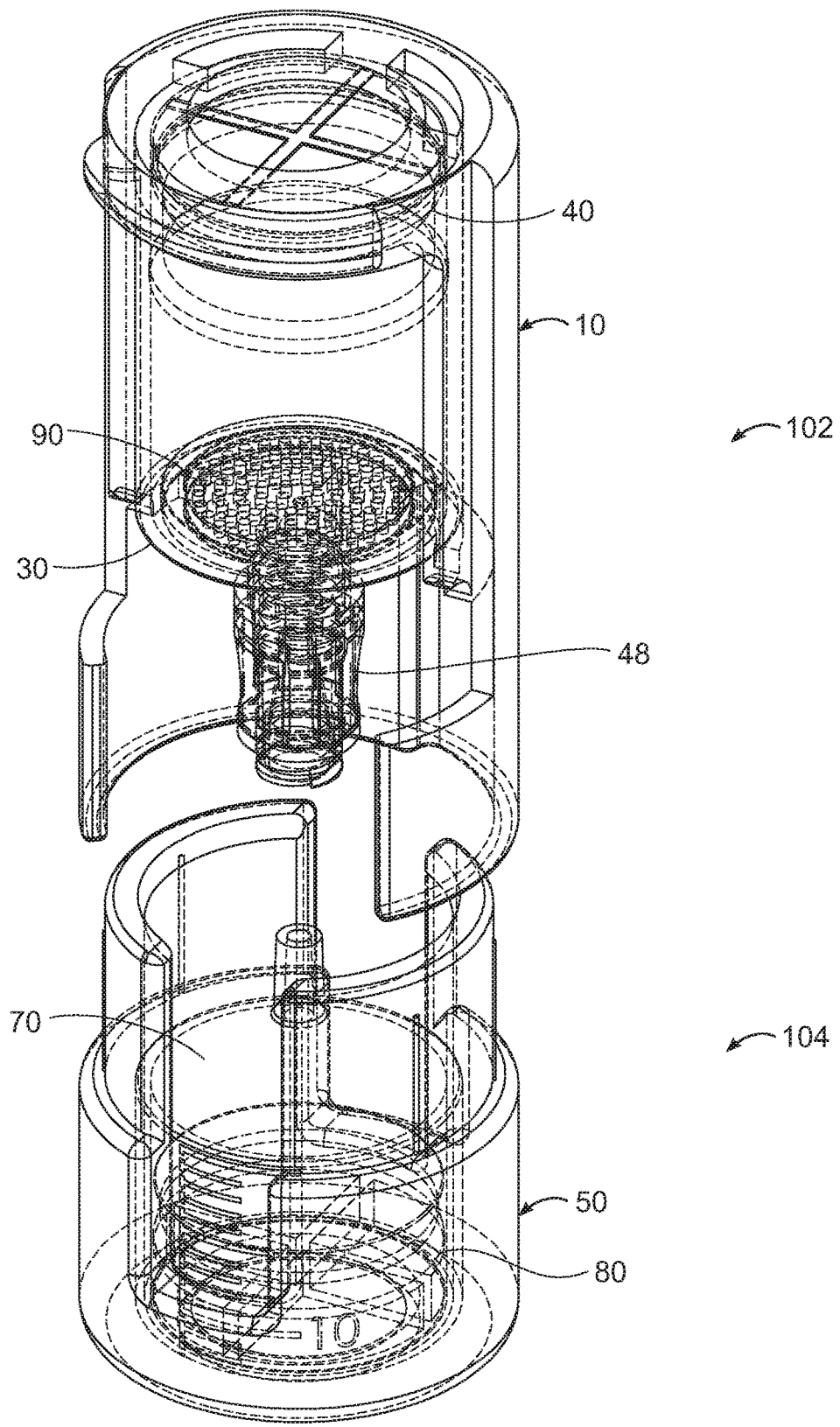
FIG. 3A is a perspective view of the two exoskeletons of FIGS. 1C and 2B with the exoskeletons and syringes disassembled.

FIG. 3A is a perspective view of the two exoskeleton assemblies 102 and 104 of FIG. 1C and FIG. 2B with the exoskeletons 10, 50 and syringes 30, 70 aligned for assembly.

FIGS. 3B and 3C illustrate the two exoskeletons and syringes assembled with the upper and lower exoskeletons each supporting a syringe. The syringes 30, 70 are connected and in fluid communication through the Luer connection 48. The exoskeletons 10, 50 are connected through a keyway mating feature. The exoskeleton 10 includes a tab 28 (FIG. 1A) keyed to fit into either of the openings 56 (FIG. 2A) of the exoskeleton 50. The two syringes 30, 70 are in fluid communication when assembled as a single structure.

As shown in FIGS. 3B and 3C, the Luer to Luer connection includes a female swabable Luer 48 at one of the syringes and a male slip fit Luer 86 at the other of the syringes.

One of the exoskeletons can include a stop and the assembled exoskeletons can create an interference fit that absorbs the force created by the centrifuge, the stop and the interference fit preventing the Luer to Luer connection from breaking during centrifugation. A stop can be provided by the inwardly facing ridges 18 of exoskeleton 10. Another stop can be provided by the outwardly facing ridge 58 of exoskeleton 50, which provide a stop for the bottom end of exoskeleton 10. The exoskeleton 50 includes ridges 68 (FIG. 2A) on an outside wall section that engages an inside wall section of exoskeleton 10, to enhance the interference fit with exoskeleton 10.

The device can include a screen 90 in the syringe 30 between the plunger 40 and the tip 32 of the syringe. The screen can have a circumference such that it creates a press fit between an inside wall of the barrel and the screen when inserted into the syringe.

Figure 4:
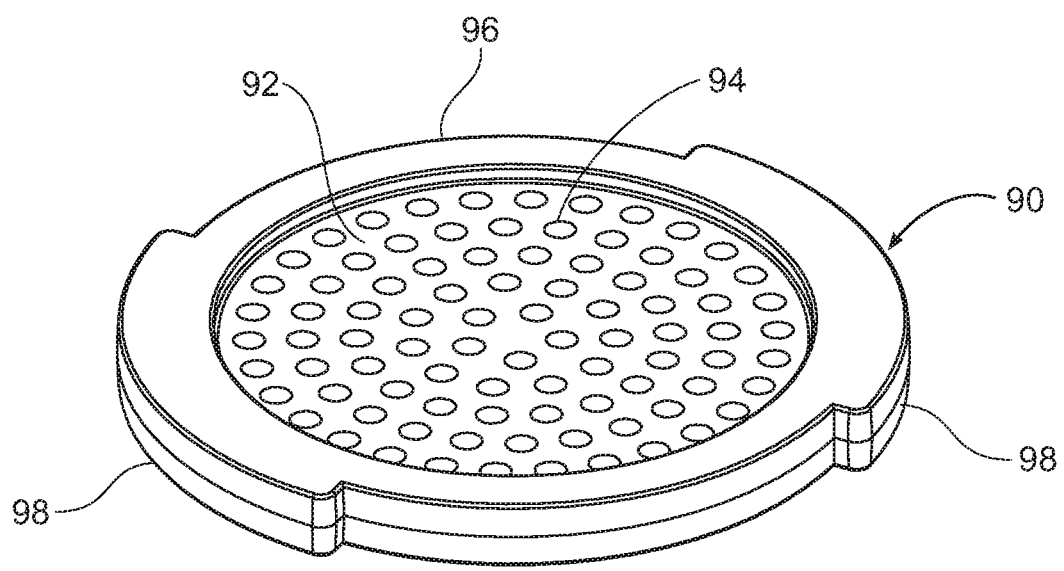
FIG. 4 is a top view of an example screen that can be used in an upper syringe so that fluid that passes from the upper syringe to a lower syringe can be filtered through the screen using the force of the centrifuge.

FIG. 4 shows an example screen 90 that can be used in an upper syringe 30 so that fluid that passes from the upper syringe to a lower syringe 70 can be filtered through the screen using the force of the centrifuge. The screen 90 includes a perforated plate 94 having a plurality of holes 92 for fluid passage. A ring 96 surrounds the plate 94. The ring 96 is sized to allow the screen 90 to be press-fit into a suitable syringe. As shown, the ring can include flanges 98 to facilitate the press fit.

FIG. 5 is a flow diagram 500 of an example method for centrifuging a physiological fluid. At 505, a first volume of a physiological fluid is placed in a first chamber of a first assembly. The first assembly can be an exoskeleton assembly including an exoskeleton supporting a syringe, as described herein, where the syringe provides the first chamber. Alternatively, the chamber can be provided by a rigid container, e.g. a glass tube or syringe, without the need for exoskeleton support. At 510, a second volume of the physiological fluid is placed in a second chamber of a second assembly. As with the first assembly, the second assembly can be an exoskeleton assembly including an exoskeleton supporting a syringe that provides the second chamber. Alternatively, the second chamber can be provided by a rigid container without exoskeleton support. The first and second assemblies are connected (515) such that the first and second chambers are in fluid communication, and the physiological fluid in the connected first and second assemblies is subjected to centrifugation (520) to collect a first fraction of the physiological fluid in the first chamber and second fraction of the physiological fluid in the second chamber. At 525, the first and second assemblies are disconnected.

The method can further include connecting (530) the first assembly to a third assembly such that the first chamber is in fluid communication with a third chamber of the third assembly, subjecting (535) the first fraction in the connected first and third assemblies to centrifugation to collect a third fraction of the physiological fluid in the third chamber and a fourth fraction of the physiological fluid in the first chamber, and disconnecting (540) the second and third assemblies.

Figure 6:
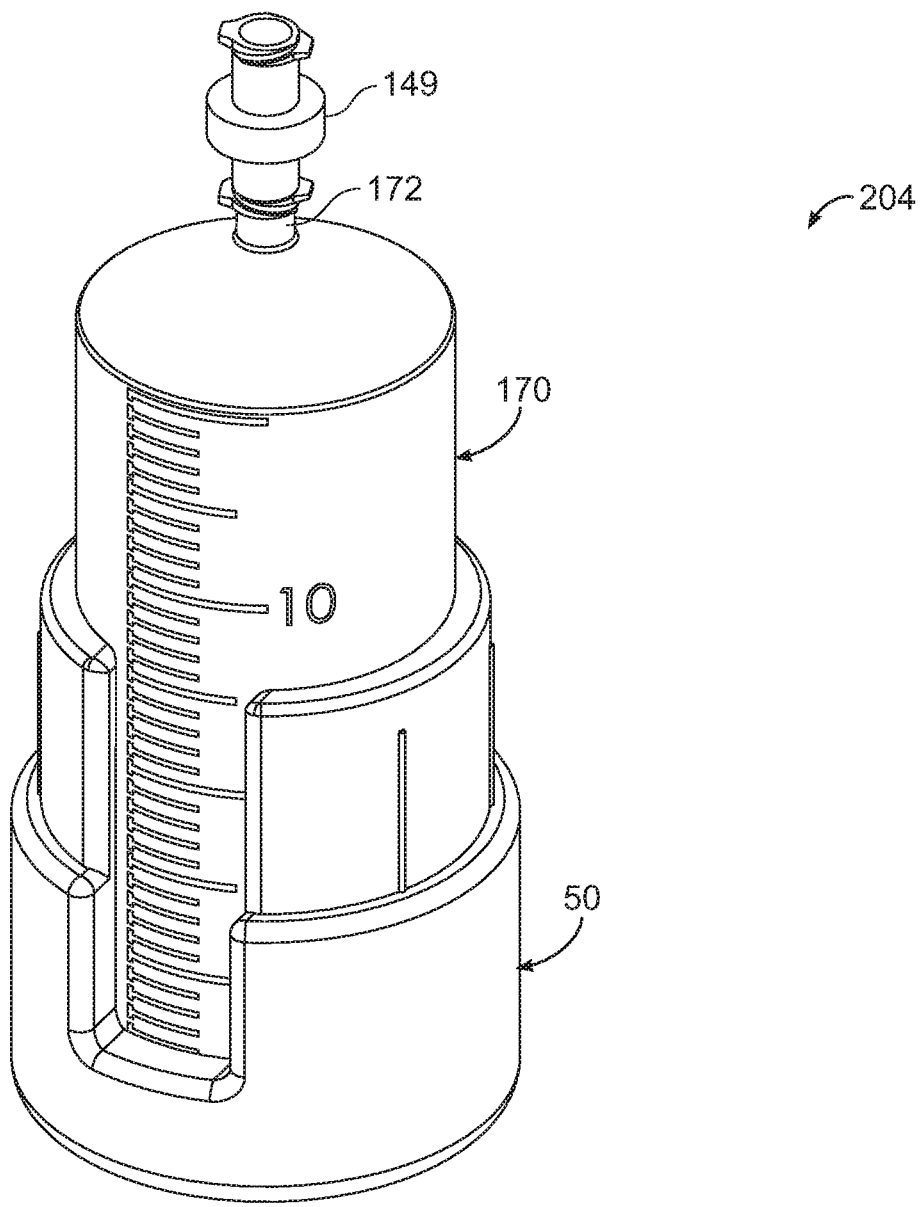
FIG. 6 is a perspective view of an example exoskeleton with a syringe holding a larger volume.

FIG. 6 is a perspective view of an example exoskeleton assembly 204 that includes exoskeleton 50 supporting a syringe 170 configured to hold a larger volume of fluid. The height of the syringe 170 from base 174 to tip 172 (FIG. 7A) is greater than the height of the exoskeleton 50. In FIG. 6, the tip 172 is shown coupled to a female-to-female Luer connector 149. Connector 149 can be used to couple to another syringe, e.g., to withdraw or introduce fluid or fluid fractions.

Figure 7A:
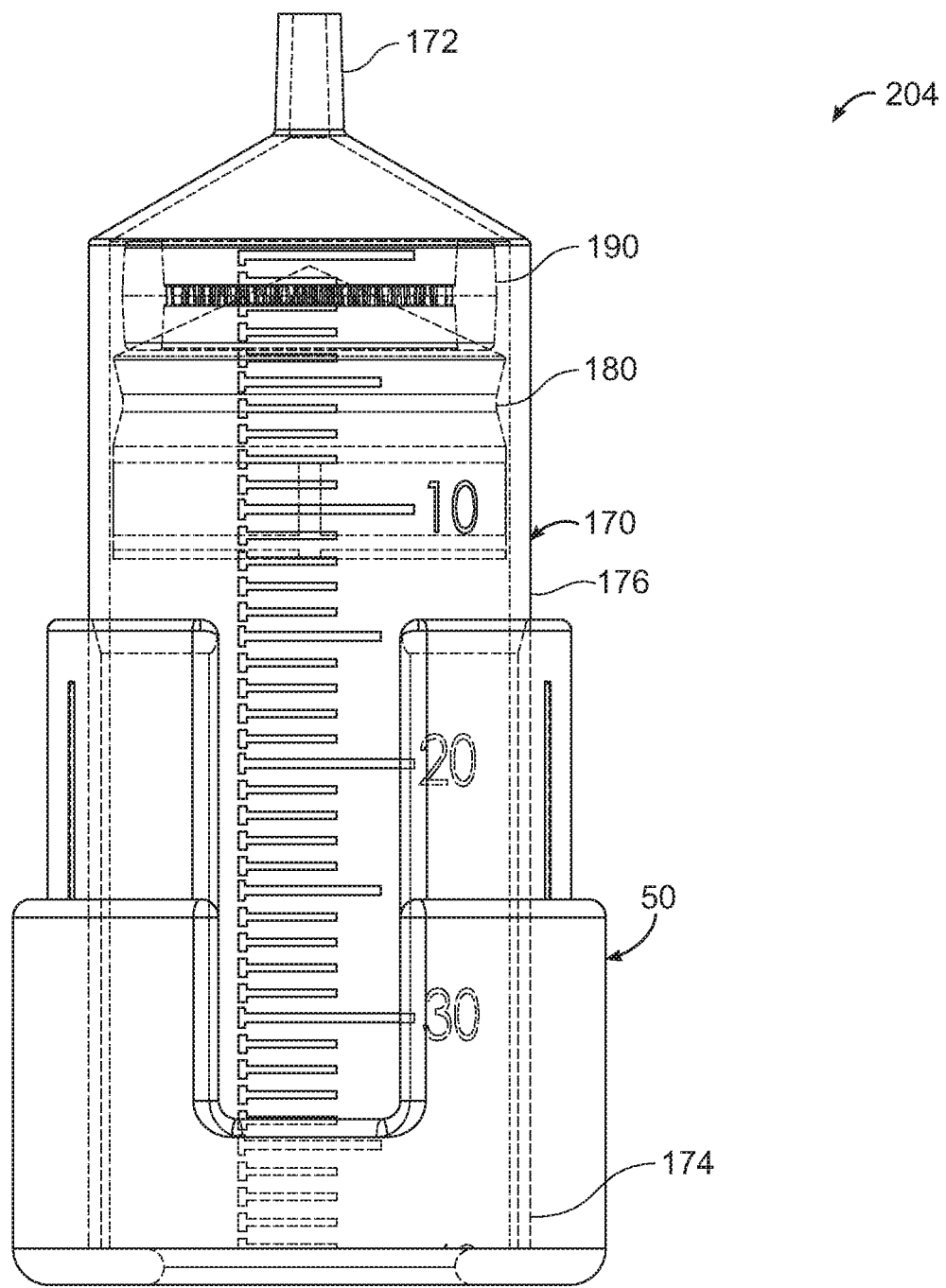
FIG. 7A is a side view of the exoskeleton of FIG. 6 with a syringe holding a larger volume illustrating a screen assembled in the syringe.

FIG. 7A shows the exoskeleton assembly 204 of FIG. 6 with syringe 170 illustrating a plunger 180 within syringe barrel 176 and a screen 190 assembled into the syringe between the plunger 180 and the tip 172.

Figure 7B:
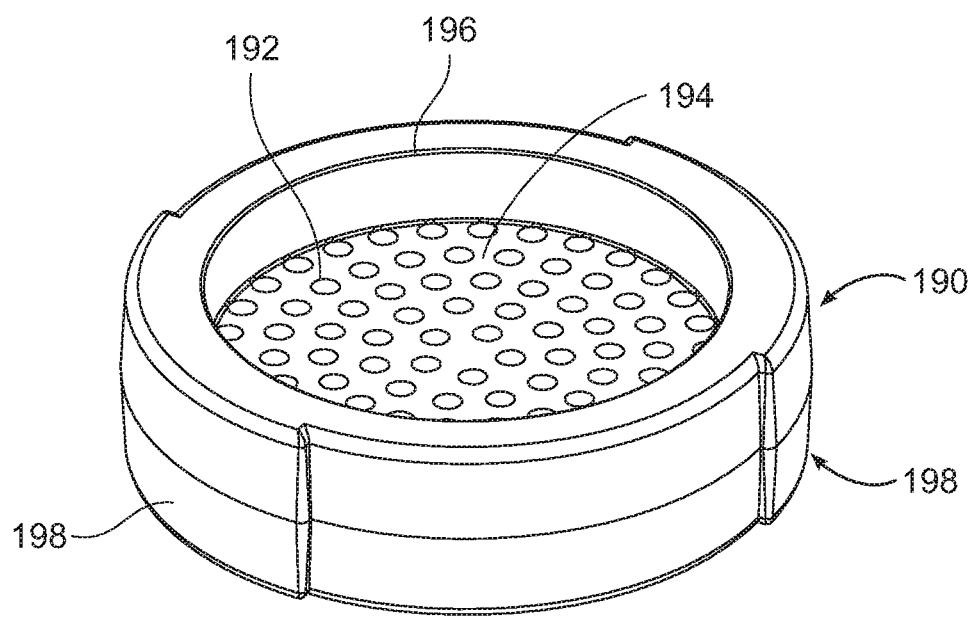
FIG. 7B is a perspective view an example screen for use with embodiments of the invention.

FIG. 7B shows details of screen 190, which can be used with embodiments of the invention. Similar to screen 90, the screen 190 includes a perforated plate 194 having a plurality of holes 192 for fluid passage. The screen includes a ring 196 that surrounds the plate 194. The ring 196 is sized to allow the screen 190 to be positioned in a syringe, e.g., syringe 170, and engage the inner wall of the syringe in a press-fit manner. As shown, the ring 196 can include flanges 198 to facilitate the press fit.

Figure 8A:
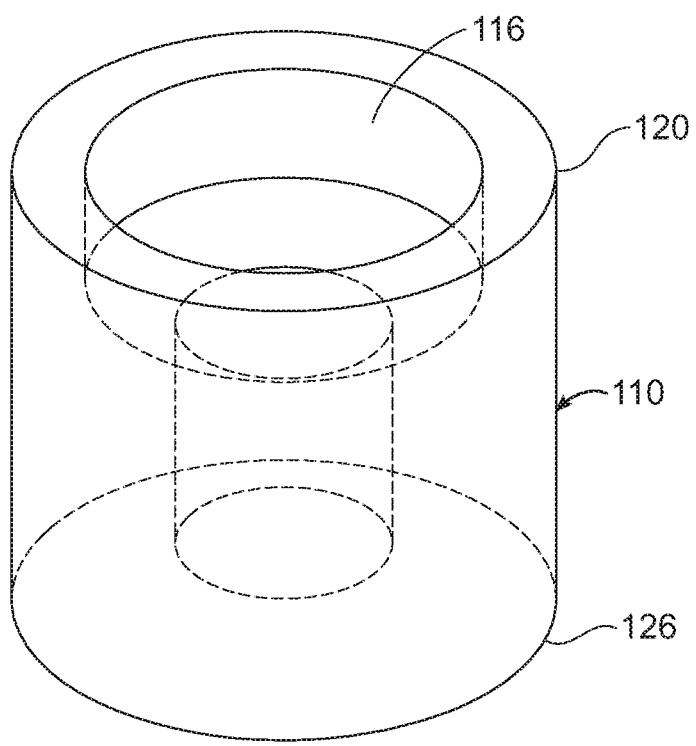
FIG. 8A is a perspective view of a detachable exoskeleton that supports a Luer tip of a syringe and the syringe around the tapered barrel nearest to the Luer tip. The exoskeleton allows the syringe to be centrifuged Luer tip down with most of the force of the centrifuge being absorbed by the syringe barrel and not the Luer tip.

FIG. 8A illustrates a detachable exoskeleton 110 that supports a Luer tip 172 of syringe 170 and the syringe around the tapered parts of the barrel nearest to the Luer tip. The exoskeleton 110 allows the syringe 170 to be centrifuged Luer tip down with most of the force of the centrifuge being absorbed by the syringe barrel 176 and not the Luer tip.

Figure 8C:
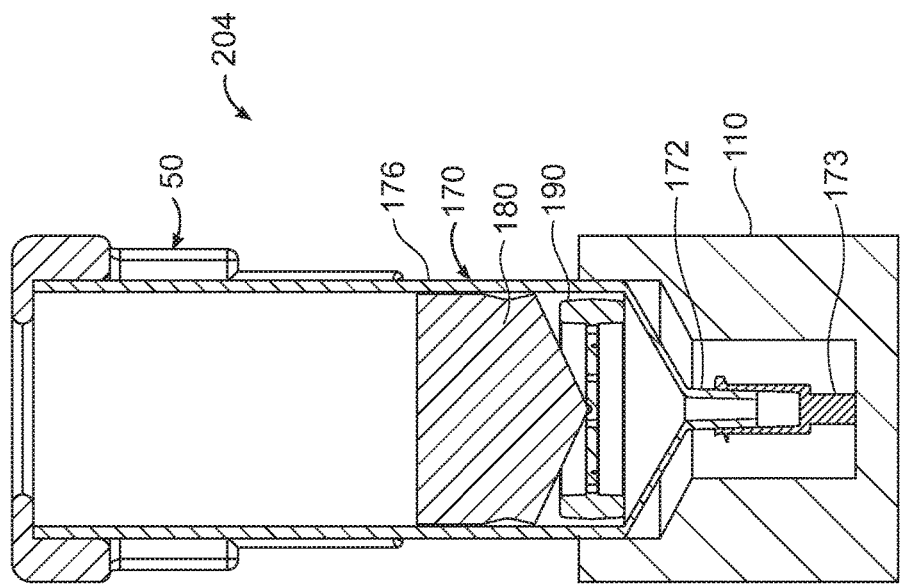
FIGS. 8B and 8C are side and sectional views, respectively, of a syringe supported by two exoskeletons, an upper exoskeleton and a lower exoskeleton.
Figure 8B:
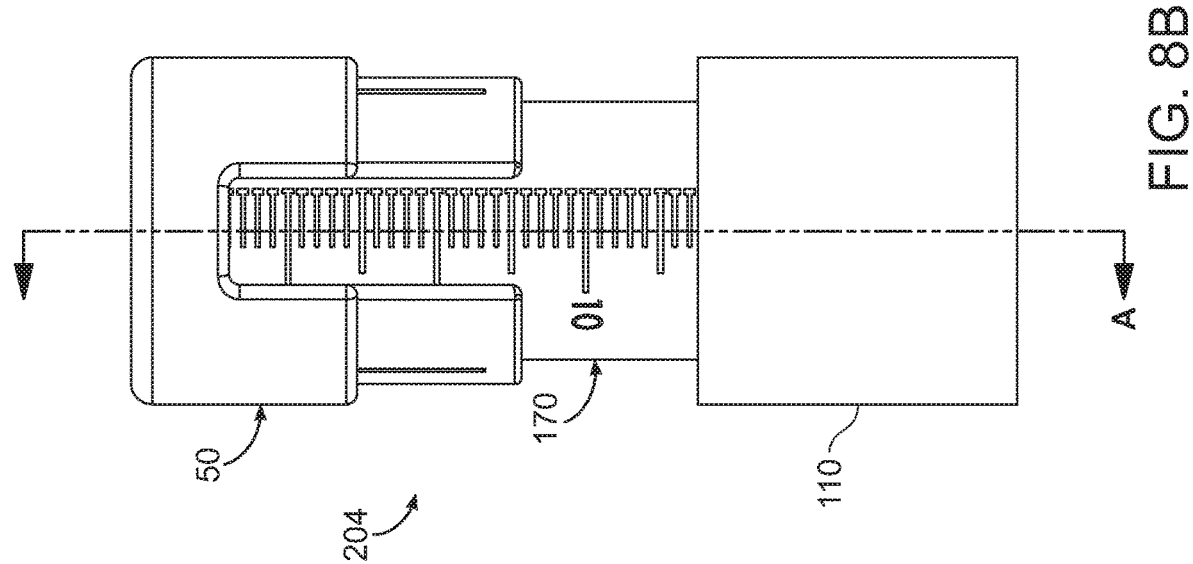

FIGS. 8B and 8C show the syringe 170 of assembly 204 supported by exoskeletons 50 and 110, where one is used as an upper exoskeleton and the other as a lower exoskeleton. The syringe tip 172 is capped with a Luer cap 173. The lower, tube-shaped exoskeleton 110 has a closed bottom 126 to support the capped tip of the syringe. The exoskeleton 110 includes an open top 120 having opening 116 to receive the barrel 176 of the syringe 170.

FIG. 9 is a flow diagram of another method for centrifuging a physiological fluid according to an example embodiment. The method includes holding (905) a physiological fluid in a syringe, the syringe including a tip, a base and a barrel extending between the tip and the base. The syringe further includes a plunger positioned within the barrel, the plunger including a plunger seal in sealing engagement with an inside wall of the barrel. The method further includes supporting (910) the syringe at least partially within an exoskeleton, the syringe being removably coupled to the exoskeleton using an interference fit, and centrifuging (915) the physiological fluid in the syringe while the syringe is supported by the exoskeleton. Depending on the configuration of the exoskeleton, the physiological fluid can be centrifuged (at 915) with the base of the syringe away from a center of a centrifuge rotor or with the tip of the syringe away from a center of a centrifuge rotor.

EXEMPLIFICATION

Example of Use: Example 1

In this example, centrifugation of blood using an embodiment of the invention is described as illustrated in FIGS.

Figure 10A:
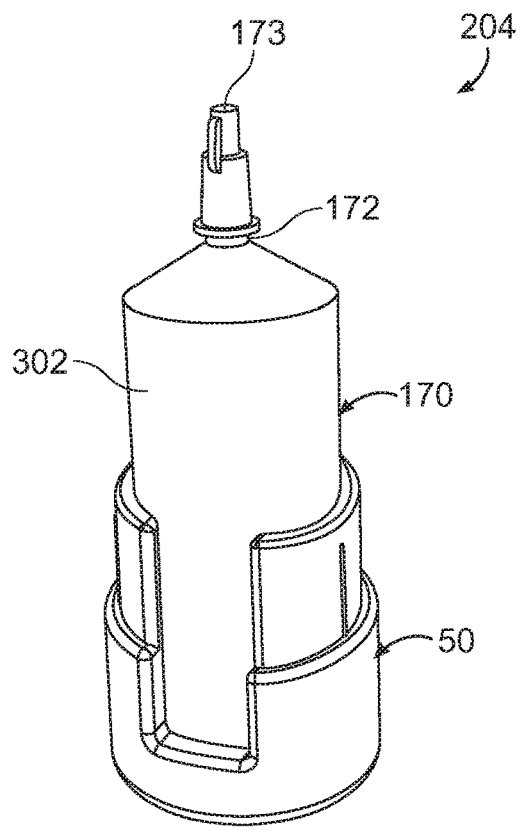
FIG. 10A is a perspective view, prior to centrifugation, of an example exoskeleton assembly including a syringe and exoskeleton, configured to create a tight press fit to hold the syringe filled with blood so that the plunger of the syringe is supported to prevent any leaking of fluid around the plunger.

10A-10E. Blood 302 is loaded into an exoskeleton assembly 204 including a modified syringe 170 with an exoskeleton 50 supporting the base of the syringe opposite to the Luer tip 172 of the syringe. FIG. 10A is a perspective view, prior to centrifugation, of the exoskeleton assembly 204 including syringe 170 and exoskeleton 50, configured to create a tight press fit to hold the syringe filled with blood so that the plunger of the syringe is supported to prevent any leaking of fluid around the plunger. The tip 172 is capped with Luer cap 173.

Figure 10B:
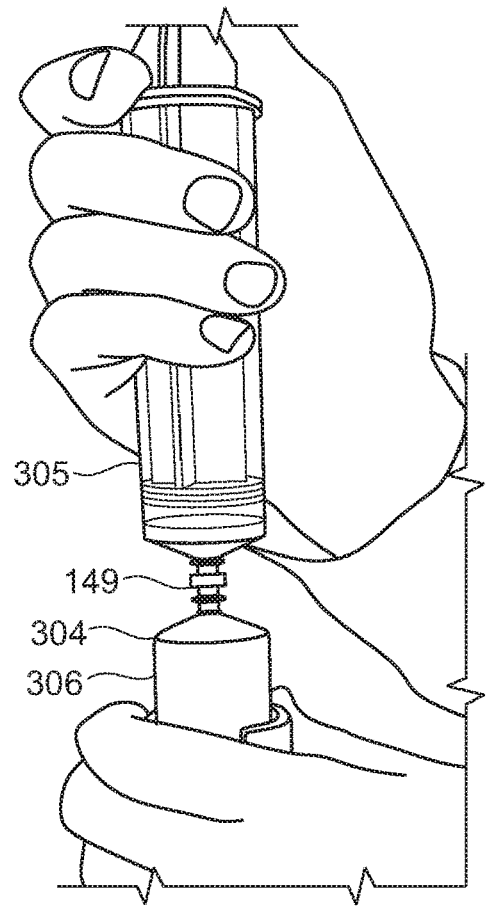
FIG. 10B is a perspective view, post first centrifugation step, of the syringe and exoskeleton of FIG. 10A, with cloudy plasma being extracted to a collection syringe.
Figure 10C:
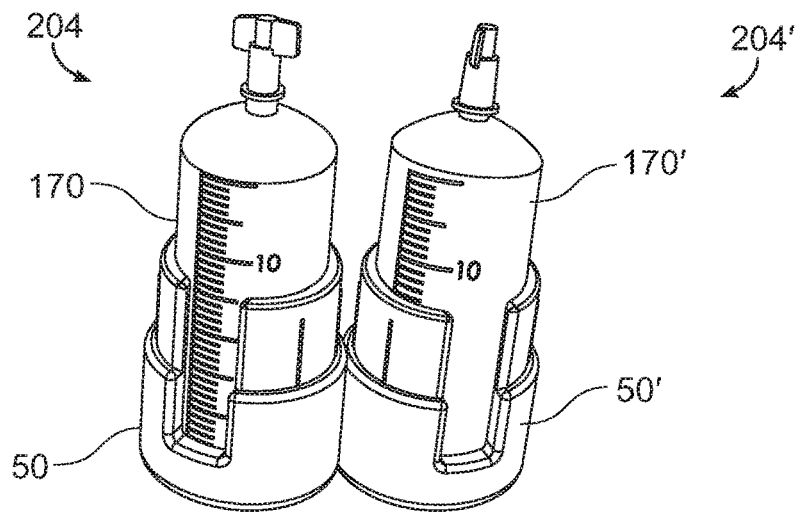
FIG. 10C is a perspective view, post first centrifugation step but prior to second centrifugation step, of cloudy plasma loaded into a second exoskeleton assembly including a second syringe supported by a second exoskeleton.

The exoskeleton assembly 204 is placed in a centrifuge for 2 minutes at 1,000 g force. The exoskeleton assembly is removed from the centrifuge and a collection syringe 305 is used to evacuate cloudy plasma 304 from the exoskeletal assembly up to the approximate demarcation line between plasma 304 and red blood cells 306. FIG. 10B is a perspective view, post first centrifugation step, of the syringe and exoskeleton of FIG. 10A, with cloudy plasma 304 being extracted to a collection syringe coupled to Luer tip 172 of the syringe via a female-female Luer connector 149. The red blood cells are discarded. The cloudy plasma is transferred to an empty exoskeleton assembly and centrifuged for 8 minutes at 1000 g. FIG. 10C is a perspective view, post first centrifugation step but prior to second centrifugation step, of cloudy plasma loaded into a second exoskeleton assembly 204' including a second syringe 170' supported by a second exoskeleton 50'.

Figure 10D:
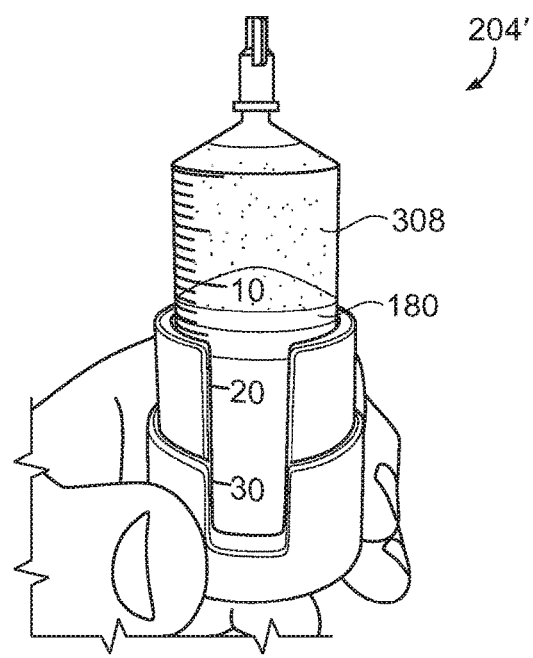
FIG. 10D is a perspective view, post second centrifugation step of the second syringe illustrating platelet poor plasma above a platelet pellet that is just above the syringe plunger.
Figure 10E:
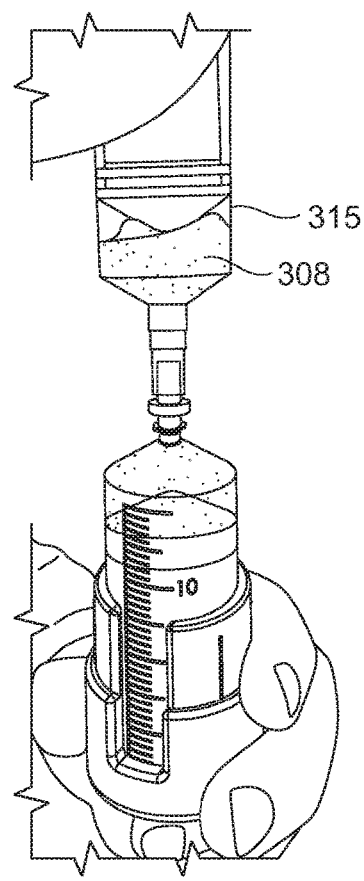
FIG. 10E is a perspective view, post second centrifugation step, of the second syringe and exoskeleton, with platelet poor plasma being extracted to a collection syringe.
Figure 10F:
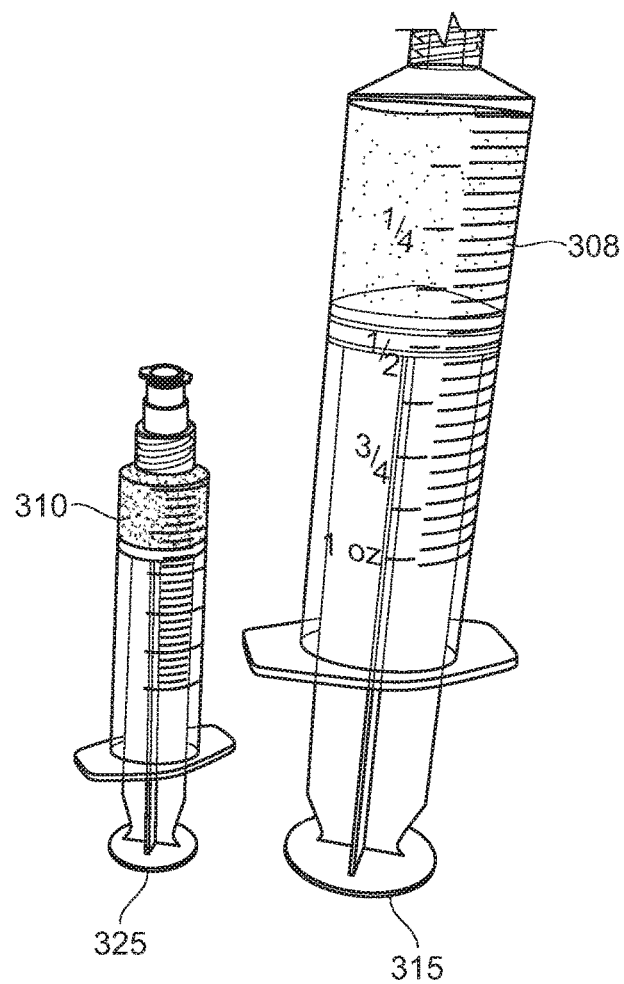
FIG. 10F is a perspective view of plasma in one (larger) collection syringe and platelets with some red cells in a second (smaller) collection syringe.

FIG. 10D is a perspective view, post second centrifugation step of the second syringe 170' illustrating platelet poor plasma 308 above a platelet pellet that is just above the syringe plunger 180. The exoskeleton assembly is removed from the centrifuge and the clear plasma above the platelets is evacuated using a collection syringe 315. FIG. 10E is a perspective view, post second centrifugation step, of the second syringe and exoskeleton, with platelet poor plasma 308 being extracted to a collection syringe 315. A separate collection syringe 325 is then used to evacuate the platelets. This fraction is often referred to as platelet rich plasma. FIG. 10F is a perspective view of plasma 308 in one (larger) collection syringe 315 and platelets 310 with some red cells in a second (smaller) collection syringe 325.

Example of Use: Example 2

Described is an example process of centrifuging marrow using an embodiment of the invention. The process is illustrated in the accompanying FIGS. 11A-11E.

FIG. 11A shows an example device including upper and lower exoskeleton assemblies 102 and 104. Each assembly includes a syringe supported by an exoskeleton 10, 50. Upper and lower syringes are both loaded with marrow 400, and are connected and in fluid communication via the Luer fitting and prior to the first centrifuge step. Additional details are described below.

Marrow aspirate 400 is loaded into a first assembly 102 containing a modified syringe with an exoskeleton 10 supporting the base of the syringe (exoskeleton assembly 1). Marrow is loaded into a second assembly 104 containing a modified syringe with an exoskeleton 50 supporting the base of the syringe (exoskeleton assembly 2). This first exoskeleton 102 also supports a portion of the exterior barrel of the syringe where the diameter of the barrel of the syringe narrows proximal to the Luer fitting and distal to the plunger, as described in references to FIGS. 1A-3C. Exoskeletal assembly 102 is connected on top of exoskeletal 104 with the Luer to Luer connection in fluid communication. Exoskeletal assembly 102 contains 3 times the volume as exoskeletal 104 or in the example shown 15 cc in the top chamber and 5 cc in the bottom chamber with the Luer to Luer connection allowing for fluid communication between the chambers. The connected assemblies are placed into a centrifuge and centrifuged for 3 minutes at 1,000 g force. The connected exoskeleton assemblies are then removed from the centrifuge.

FIG. 11B illustrates the connected assemblies of FIG. 11A after the first centrifugation step. In the lower assembly 104 are red blood cells 406 and in the upper assembly 102 are red blood cells 406 on the bottom and on top of that cloudy yellow plasma 404 (see also FIG. 11C).

The bottom exoskeleton assembly 104 now contains primarily red blood cells and is removed and can be discarded. The upper exoskeletal assembly 102 contains the remaining fraction of red blood cells, platelets, white blood cells, and plasma that was not discarded with the lower exoskeletal assembly. The upper exoskeletal assembly 102 is then attached to a second lower exoskeletal assembly 104', which is empty but otherwise identical to the first lower exoskeleton assembly 104. The syringes are connected by Luer to Luer connection and are in fluid communication with each other. FIG. 11C illustrates the device after the first centrifugation step and after the first lower assembly 104 containing primarily red cells has been removed and discarded and replaced by an identical empty assembly 104'. The lower assembly 104' is connected to the upper assembly containing red blood cells 406 on the bottom and on top of that white cells and plasma and then cloudy yellow plasma 404 with the Luer fittings in fluid communication. This entire structure is then placed back into the centrifuge.

This structure with an empty bottom assembly is centrifuged for 8 minutes at 1000 g. The structure is removed from the centrifuge and the platelet rich plasma, white cells and some red cells are in the lower exoskeletal assembly and only primarily platelet poor plasma is in the upper assembly. The lower exoskeleton assembly, after the second centrifugation step, contains what is referred to as 'buffy coat' and some red blood cells. This fraction can now be removed for clinical use. The platelet rich plasma in the syringe of the lower assembly 104 is transferred to a collection syringe using a Luer connection. The platelet poor plasma in the syringe of the upper assembly is typically discarded but can also evacuated using a collection syringe for further use.

Figure 11D:
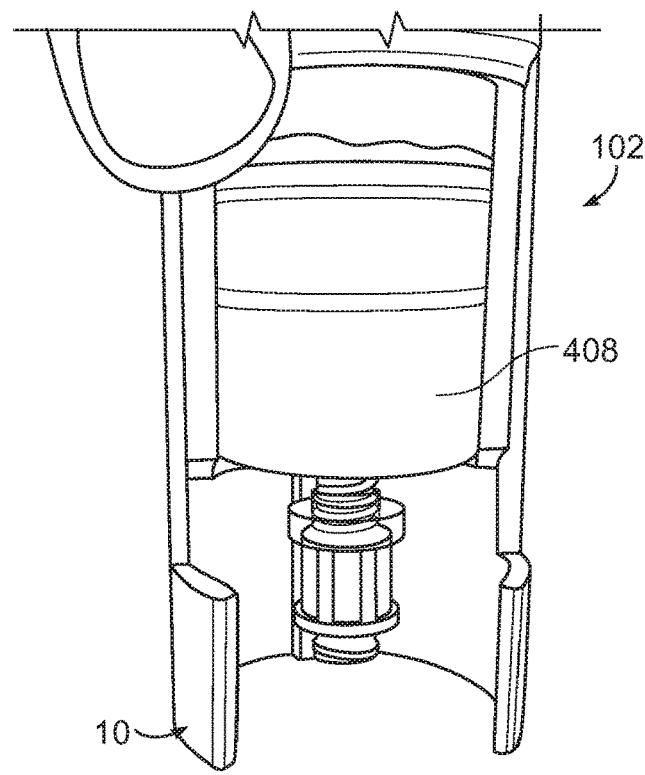
FIGS. 11D and 11E are perspective views of the upper exoskeleton assembly and lower exoskeleton assembly, respectively, after the second centrifugation step and after the assemblies have been disconnected from each other. Platelet rich plasma, white cells and some red cells are in the lower exoskeleton assembly (FIG. 11E) and primarily platelet poor plasma is in the upper exoskeleton assembly (FIG. 11D).
Figure 11E:
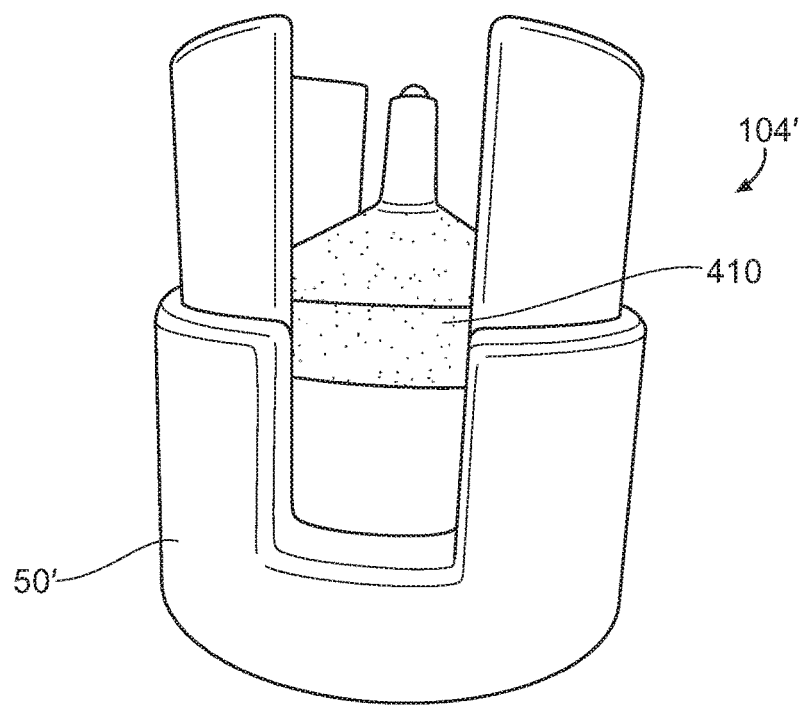

FIGS. 11D and 11E illustrate the upper exoskeleton assembly 102 and lower exoskeleton assembly 104', respectively, after the second centrifugation step and after the assemblies have been disconnected from each other. Platelet rich plasma 410, white cells and some red cells are in the lower exoskeleton assembly 104' (FIG. 11E) and primarily platelet poor plasma 408 is in the upper exoskeleton assembly 102 (FIG. 11D). The platelet rich plasma can be transferred from the lower exoskeleton assembly to a collection syringe using a Luer connection. The platelet poor plasma can be discarded or can also be evacuated using a collection syringe for use. For example, the entire upper exoskeleton assembly 102 including the platelet poor plasma in the upper syringe can be discarded. Alternatively, portions of the assembly, such as the exoskeleton 10, may be separated, sterilized, and re-used, while other portions, such as the syringe, may be discarded after a single use.

Example of Use: Example 3

In this example, centrifugation of fat aspirate using an embodiment of the invention is described and illustrated in the accompanying figures, FIGS. 12A-12E.

Figure 12B:
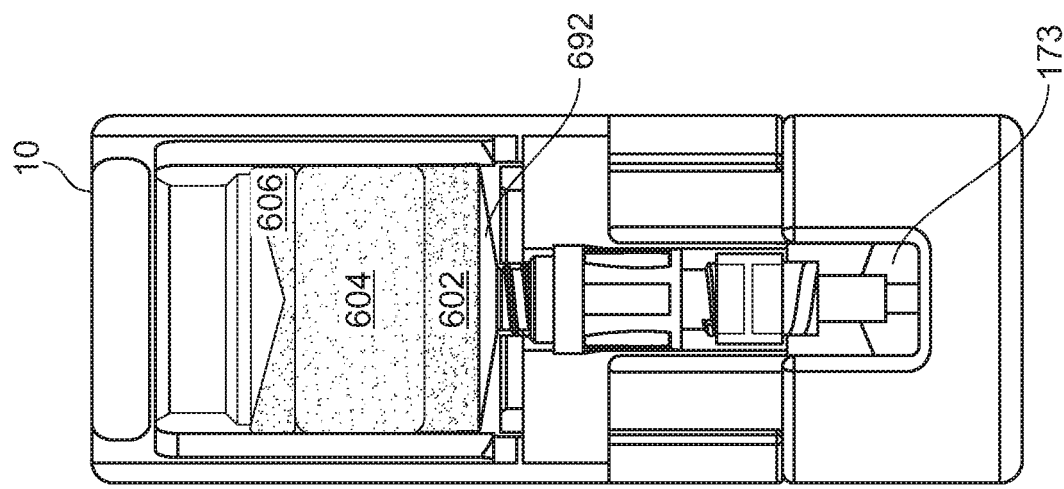
FIG. 12B is a side view of the device of FIG. 12A illustrating fat aspirate in the syringe following a first centrifugation step.
Figure 12A:
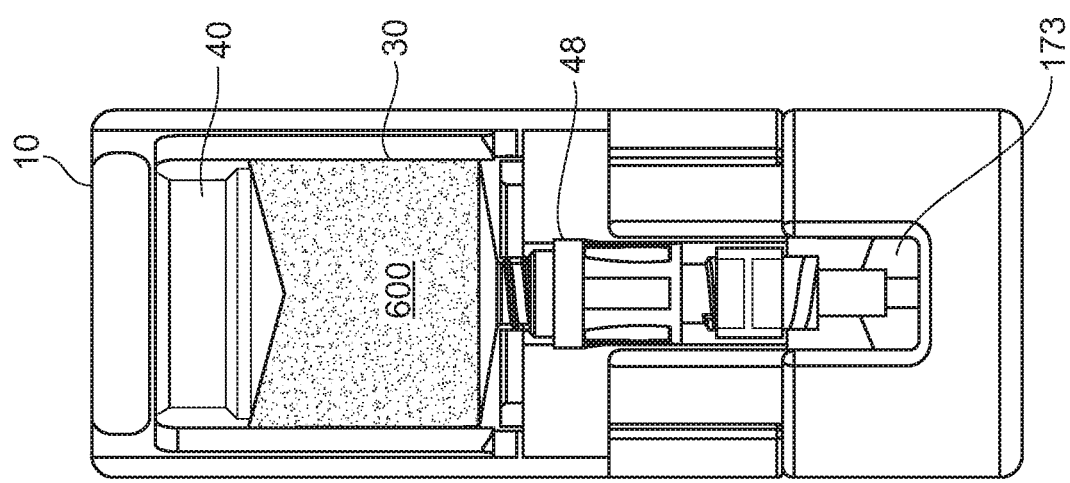
FIG. 12A is a side view of an example device for centrifuging fat aspirate illustrating fat aspirate (adipose aspirate) loaded into a syringe of an exoskeleton assembly.

FIG. 12A is a side view of an example device for centrifuging fat aspirate. Fat aspirate 500 (adipose aspirate) is loaded into an assembly 102 including a modified syringe 30 with an exoskeleton 10 supporting the base of the syringe opposite to the Luer tip. The exoskeleton 10 also supports a portion of the exterior barrel of the syringe where the diameter of the barrel of the syringe narrows proximal to the Luer fitting and distal to the plunger. A closed ended male Luer fitting 173 (e.g., Luer cap) is assembled into the swab-able female Luer fitting 48 in the modified syringe in the exoskeleton. This assembly can be placed into a centrifuge (see also FIG. 11D and associated description). Optionally, as shown in FIG. 12A, a bottom support structure 650 can be assembled onto the bottom of the exoskeleton assembly 10 to prevent excess force being applied to the Luer tip. The support structure 650 can be the same as or similar to the exoskeleton 50 shown in FIG. 2A. The assembly is centrifuged for 1 minute at 1,000 g force, Luer tip facing away from the center of the centrifuge rotor.

Figure 12C:
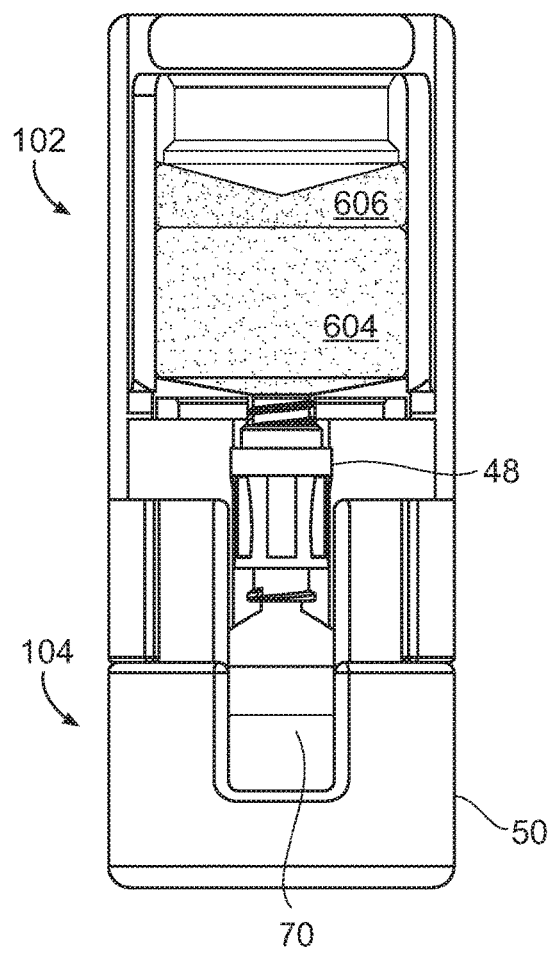
FIG. 12C is a side view of the device of FIG. 12B in which the bottom structure has been replaced with a second exoskeleton assembly including a syringe. The second exoskeletal assembly is connected to the first assembly with the Luer to Luer connection such that the upper and lower syringes are in fluid communication. The device can be placed into a centrifuge for a second centrifugation step.

FIG. 12B illustrates fat aspirate in the syringe 30 following a first centrifugation step. Upon removing the assembly from the centrifuge, the Luer cap 173 is removed and a syringe is attached to the Luer fitting and the tumescent fluid and red cells 602 are removed until the fat 604 is against the bottom of the syringe. The fat graft is now against a screen 690 that is in the bottom of the syringe. A second exoskeletal assembly 104 is connected to the first assembly 102 with the Luer to Luer connection in fluid communication. This second assembly 104 includes a modified syringe 70 with an exoskeleton 50 supporting the base of the syringe distal to the Luer tip. FIG. 12C shows the device of FIG. 12B in which the bottom structure has been replaced with a second exoskeleton assembly 104. The first exoskeletal assembly 102 can contain 3 times the volume of the second exoskeleton assembly. In the example shown, the volume is 15 cc in the top chamber and 5 cc in the bottom chamber with the Luer to Luer connection allowing for fluid communication between the chambers. The entire structure of connected exoskeleton assemblies is placed into a centrifuge and spun for 3 minutes at 1,000 g force. The connected exoskeleton assemblies are then removed from the centrifuge.

Figure 12D:
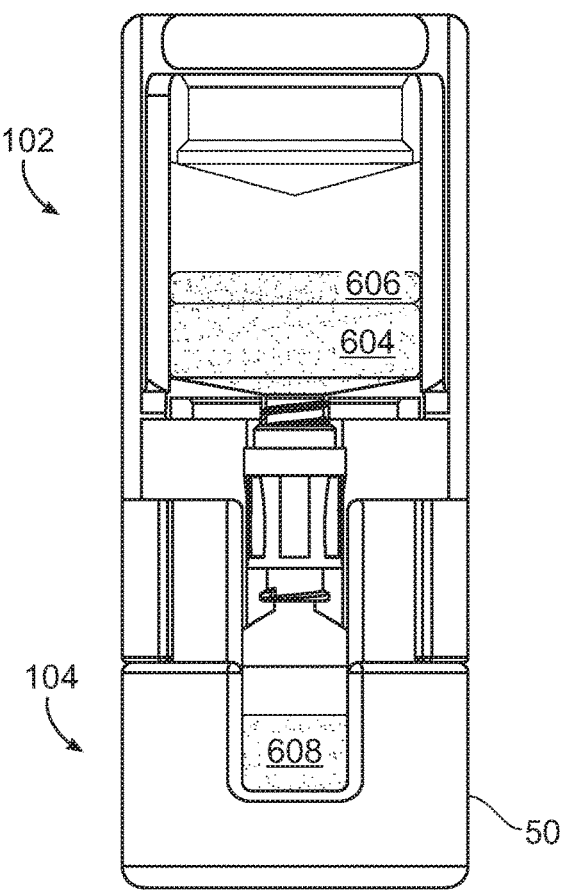
FIG. 12D is a side view of the exoskeleton assemblies of FIG. 12C after the second centrifugation step. The bottom exoskeleton assembly now contains the fat graft that has been filtered through a screen at the bottom of the upper syringe. The upper exoskeletal assembly contains the remaining fraction of fat that would not pass through the screen as well as any lower density oil.

FIG. 12D shows the exoskeleton assemblies 102, 104 after the second centrifugation step. The bottom exoskeleton assembly 104 now contains the fat graft that has been filtered through the screen 690 at the bottom of the upper syringe. The upper exoskeletal assembly 102 contains the remaining fraction of fat 604 that would not pass through the screen and any lower density oil 606 present in the fat aspirate. The two assemblies are separated and the fat graft can be transferred to a collection syringe.

Figure 12E:
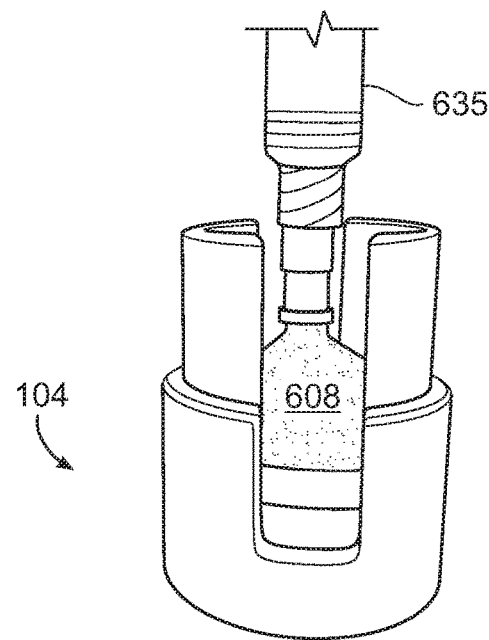
FIG. 12E illustrates the bottom exoskeleton assembly separated from the upper assembly. The fat graft is transferred from the bottom assembly to a collection syringe.

FIG. 12E illustrates the bottom exoskeleton assembly 104 separated from the upper assembly and containing the fat graft 608 that has been filtered through the screen 690 at the bottom of the upper syringe. The fat graft is transferred from the bottom assembly to a collection syringe 635 using a Luer fitting and negative pressure generated with the plunger of the collection syringe.

The components for harvesting and centrifuging a biological fluid can be assembled into a kit of various configurations. Generally, the kit contains three sets of tools to accomplish three things: 1) to source tissue from patient such as blood, marrow or fat; 2) components to perform a first centrifugation step and 3) components to perform a second centrifugation step. The three sets can be packaged in three separated pouches and can be sterilization, as appropriate. Components to be placed in a centrifuge are usually supplied in pairs, e.g., a pair of exoskeleton assemblies, to be centrifuged together to ensure proper balancing of the centrifuge. Providing and using pairs of components avoids the need to provide and use dummy counterweights. An example kit for centrifuging a biological fluid is illustrated in FIG. 13.

Figure 13:
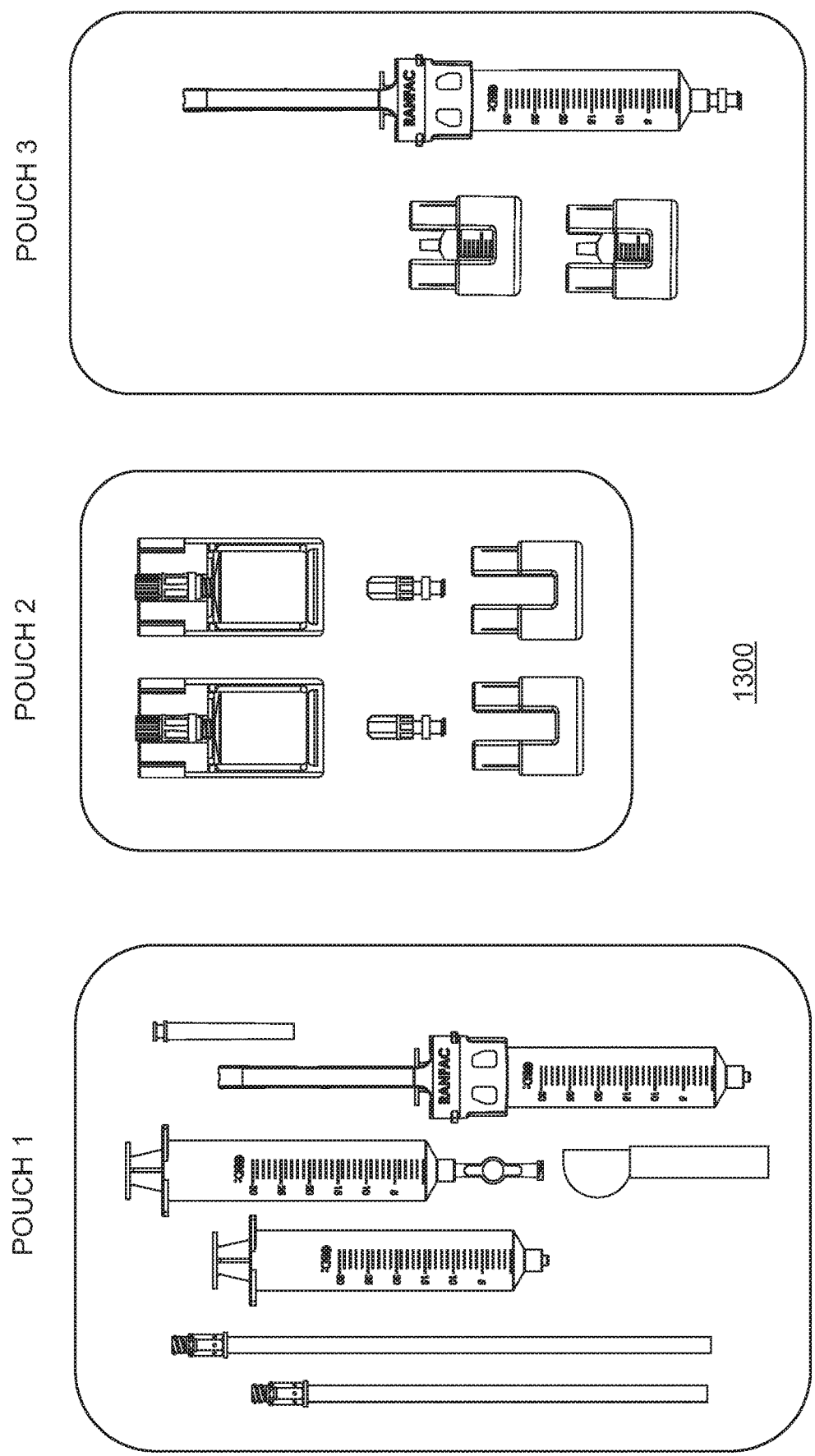
FIG. 13 illustrates and example kit for centrifuging a biological fluid.

FIG. 13 illustrates and a kit 1300 for centrifuging fat aspirate. The kit is organized in three pouches: Pouch 1 includes the tools to aspirate fat to be used in the device as described in Example 3. The tools include a scalpel, an infiltrator cannula, an aspiration cannula, and syringes to inject and aspirate. Pouch 2 includes the tools to perform a first centrifugation step as described in Example 3. The tools include two upper exoskeleton assemblies, each including a syringe and an exoskeleton, two winged Luer caps, and two lower support structures. Pouch 3 includes the tools to perform a second centrifugation step as described in Example 3. The tools include two lower exoskeleton assemblies, each including a syringe and an exoskeleton, and one or more collection syringes.

Prior approaches to centrifuging physiological fluids have used a funnel-shaped insert positioned in a centrifugation container to separate cell fractions. Embodiments of the present invention do not require such an insert. Examples of prior approaches using inserts are described in the following published applications, the teaching of which are incorporated herein by reference in their entirety:

Cell separation methods and apparatus are described in International Application No. PCT/US2006/042237, filed on Oct. 27, 2006 and published on May 3, 2007 as WO2007/050986 A1. Cell concentration devices and methods are described in International Application No. PCT/US2014/013636, filed on Jan. 29, 2014 and published on Aug. 7, 2015 as WO2014/120797 A1. Apparatus and methods for aspirating and separating components of different densities from a physiological fluid containing cells are described in International Application No. PCT/US2010/036696, filed on May 28, 2010 and published on Dec. 2, 2010 as WO2010/138895 A2.

Physiological fluids, such as bone marrow, can be aspirated using double-cannula needle assemblies. Examples of such approaches are described in the following patent applications, the teachings of which are incorporated herein by reference in their entirety:

Apparatus and methods for aspirating and separating components of different densities from a physiological fluid containing cells are described in International Application No. PCT/US2010/036696, filed on May 28, 2010 and published on Dec. 2, 2010 as WO2010/138895 A2. Apparatus and methods for aspirating tissue are described in International Application No. PCT/US2013/067358, filed on Oct. 29, 2013 and published on May 8, 2014 as WO2014/070804 A1. An aspiration device and associated method including an introducer needle assembly, an aspiration needle assembly and a screw assembly are described in International Application No.: PCT/US2015/011614, filed on Jan. 15, 2015 and published on Jul. 23, 2015 as WO2015/109100 A1. An aspiration device and method including an introducer cannula, an aspiration cannula and a mechanism (e.g., a screw assembly) to move the cannulae are described in U.S. application Ser. No. 14/885,821, filed on Oct. 16, 2015 and published on Apr. 21, 2016 as US 2016/0106462 A1.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A device for centrifuging a physiological fluid, the device comprising:
   a syringe including a tip, a base and a barrel extending between the tip and the base to hold a physiological fluid, the syringe including a plunger positioned within the barrel, the plunger including a plunger seal in sealing engagement with an inside wall of the barrel, a diameter of the barrel narrowing between the tip and the plunger; and
   an exoskeleton to support the syringe at least partially within the exoskeleton for use in a centrifuge, the syringe being removably coupled to the exoskeleton using an interference fit, the exoskeleton including one or more inwardly protruding ridges to support the barrel of the syringe where the diameter of the barrel of the syringe narrows between the tip and the plunger, the exoskeleton including a sidewall with a longitudinal opening to facilitate one or more of viewing the syringe, accessing the syringe, and loading and unloading the syringe into and from the exoskeleton, the opening sized to allow the exoskeleton to snap fit around the barrel of the syringe.

2. A device according to claim 1, wherein the plunger is without a handle attached to the plunger.

3. A device according to claim 1, wherein the exoskeleton is configured to support the syringe while the g-force generated by the centrifuge is between 30 g and 3000 g.

4. A device according to claim 1, wherein the sidewall is configured to support the base and plunger of the syringe.

5. A device according to claim 1, wherein the exoskeleton includes an inner wall that fits tightly around a circumference of the barrel at the base of the syringe, the inner wall of the exoskeleton, when the syringe is subjected to elevated g-force from the centrifuge, supporting the base and plunger in a manner that prevents distortion of the syringe barrel that prevents fluid from leaking around the seal created between the inside wall of the barrel and the plunger seal.

6. A device according to claim 1, wherein the one or more inwardly protruding ridges of the exoskeleton support a portion of the barrel of the syringe where the diameter of the barrel of the syringe narrows between the tip and the plunger so that, when the syringe is subjected to elevated g-force from a centrifuge, the force of the centrifuge is absorbed by the exoskeleton and barrel of the syringe and not the tip of the syringe.

7. A device according to claim 1, wherein the exoskeleton is tube shaped and defines a central lumen for receiving the syringe.

8. A device according to claim 7, wherein the height of the lumen of the tube-shaped exoskeleton is greater than the height of the syringe measured from the syringe base to the syringe tip so that when the syringe is assembled into the exoskeleton at least one longitudinal section of the syringe is fully encompassed within the exoskeleton.

9. A device according to claim 7, wherein the syringe tip is capped and the tube-shaped exoskeleton has a closed bottom to support the capped tip of the syringe and an open top to receive the barrel of the syringe.

10. A device according to claim 7, wherein the tube-shaped exoskeleton comprises two separate parts that are sized and shaped to be assembled onto the syringe at opposite ends of the syringe, one part configured to support the barrel of the syringe and the other part configured to support the tip of the syringe.

11. A device according to claim 7, wherein the tube-shaped exoskeleton has a stop formed by ridges facing inwardly to support at least a portion of the barrel of the syringe near the tip where the diameter of the barrel is tapered.

12. A device according to claim 1, wherein the device comprises two exoskeletons and two syringes, each exoskeleton supporting one of the two syringes during centrifugation, the exoskeletons connectable to each other through a keyway mating feature, whereby the two syringes and exoskeletons are assembled to a single structure with the syringes connected by a Luer to Luer connection.

13. A device according to claim 12, wherein the Luer to Luer connection includes a female swabable Luer at one of the syringes and a male slip fit Luer at the other of the syringes.

14. A device according to claim 12, wherein one of the exoskeletons includes a stop and the assembled exoskeletons create an interference fit that absorbs the force created by the centrifuge, the stop and the interference fit preventing the Luer to Luer connection from breaking during centrifugation.

15. A device according to claim 12, wherein the two syringes are in fluid communication when assembled as a single structure.

16. A device according to claim 1, wherein the exoskeleton includes a base having a hole through the exoskeleton to provide access to the plunger of the syringe, the hole sized such that the plunger cannot pass through the hole.

17. A device according to claim 1, further including a screen in the syringe between the plunger and the tip of the syringe.

18. A device according to claim 17, wherein the screen has a circumference such that it creates a press fit between the inside wall of the barrel and the screen when inserted into the syringe.

19. A method for centrifuging a physiological fluid, the method comprising:
   holding a physiological fluid in a syringe, the syringe including a tip, a base and a barrel extending between the tip and the base, the syringe including a plunger positioned within the barrel, the plunger including a plunger seal in sealing engagement with an inside wall of the barrel, a diameter of the barrel narrowing between the tip and the plunger;
   supporting the syringe at least partially within an exoskeleton, the syringe being removably coupled to the exoskeleton using an interference fit, the exoskeleton including one or more inwardly protruding ridges to support the barrel of the syringe where the diameter of the barrel of the syringe narrows between the tip and the plunger, the exoskeleton including a sidewall with a longitudinal opening to facilitate one or more of viewing the syringe, accessing the syringe, and loading and unloading the syringe into and from the exoskeleton, the opening sized to allow the exoskeleton to snap fit around the barrel of the syringe; and
   centrifuging the physiological fluid in the syringe supported by the exoskeleton.

20. The method of claim 19, wherein the physiological fluid is centrifuged with the base of the syringe away from a center of a centrifuge rotor.

21. The method of claim 19, wherein the physiological fluid is centrifuged with the tip of the syringe away from a center of a centrifuge rotor.

22. A device for centrifuging a physiological fluid, the device comprising:

a syringe including a tip, a base and a barrel extending between the tip and the base to hold a physiological fluid, the syringe including a plunger positioned within the barrel, the plunger including a plunger seal in sealing engagement with an inside wall of the barrel; and an exoskeleton to support the syringe at least partially within the exoskeleton for use in a centrifuge, the exoskeleton defining a central lumen for receiving the syringe, the syringe being removably coupled to the exoskeleton using an interference fit, the exoskeleton comprising two separate parts that are sized and shaped to be assembled onto the syringe at opposite ends of the syringe, one end being at the tip of the syringe and the other end being at the base of the syringe, one part of the exoskeleton being tube shaped and configured to support the barrel of the syringe during centrifugation and the other part of the exoskeleton configured to support the tip of the syringe during centrifugation, the exoskeleton including a sidewall with a longitudinal opening to facilitate one or more of viewing the syringe, accessing the syringe, and loading and unloading the syringe into and from the exoskeleton, the opening sized to allow the exoskeleton to snap fit around the barrel of the syringe.

23. A device for centrifuging a physiological fluid, the device comprising:

a first syringe including a Luer tip, a base and a barrel extending between the tip and the base to hold a first volume of a physiological fluid, the first syringe including a plunger positioned within the barrel and in sealing engagement with an inside wall of the barrel;

a first exoskeleton to support a circumference of the barrel at the base of the first syringe so that the first syringe, when subjected to elevated g-force from a centrifuge, is supported by the first exoskeleton that prevents distortion of the barrel to prevent fluid from leaking around the sealing engagement between the inside wall of the barrel and the plunger of the first syringe, the first exoskeleton including a stop facing inwardly to support a portion of the barrel where the diameter of the barrel of the first syringe narrows between the Luer tip and the plunger;

a second syringe including a Luer tip, a base and a barrel extending between the tip and the base to hold a second volume of the physiological fluid, the second syringe including a plunger positioned within the barrel and in sealing engagement with an inside wall of the barrel; and a second exoskeleton to support a circumference of the barrel at the base of the second syringe so that the second syringe, when subjected to elevated g-force from the centrifuge, is supported by the second exoskeleton that prevents distortion of the barrel to prevent fluid from leaking around the sealing engagement between the inside wall of the barrel and the plunger of the second syringe, the first and second syringes and the first and second exoskeletons sized and shaped to be assembled into a single structure with the syringes connected by a Luer to Luer connection.

24. A device according to claim 23, wherein the first exoskeleton includes a sidewall with a longitudinal opening to facilitate one or more of viewing the first syringe, accessing the first syringe, and loading and unloading the first syringe into and from the first exoskeleton, the opening sized to allow the first exoskeleton to snap fit around the barrel of the first syringe.

* * * * *

UNITED STATES PATENT AND TRADEMARK OFFICE
CERTIFICATE OF CORRECTION

PATENT NO.         : 12,134,092 B2
APPLICATION NO.    : 16/767863
DATED              : November 5, 2024
INVENTOR(S)        : Andrew McGillicuddy Page 1 of 1

It is certified that error appears in the above-identified patent and that said Letters Patent is hereby corrected as shown below:

On the Title Page

Please add Item (60) Related U.S. Application Data as follows:
-- Provisional application No. 62/592,798, filed on November 30, 2017. --

Signed and Sealed this
Nineteenth Day of August, 2025

Coke Morgan Stewart
*Acting Director of the United States Patent and Trademark Office*